United States Patent
Matsumoto et al.

(10) Patent No.: US 11,399,786 B2
(45) Date of Patent: Aug. 2, 2022

(54) X-RAY DIAGNOSIS APPARATUS

(71) Applicant: Canon Medical Systems Corporation, Otawara (JP)

(72) Inventors: Masanori Matsumoto, Nasushiobara (JP); Yusuke Narabu, Nasushiobara (JP); Yoshiyuki Sato, Nasushiobara (JP); Katsuie Ikawa, Nasushiobara (JP); Takeo Matsuzaki, Nasushiobara (JP)

(73) Assignee: Canon Medical Systems Corporation, Otawara (JP)

(*) Notice: Subject to any disclaimer, the term of this patent is extended or adjusted under 35 U.S.C. 154(b) by 0 days.

(21) Appl. No.: 16/376,342

(22) Filed: Apr. 5, 2019

(65) Prior Publication Data
US 2019/0307408 A1 Oct. 10, 2019

(30) Foreign Application Priority Data
Apr. 9, 2018 (JP) .............................. JP2018-074890

(51) Int. Cl.
*A61B 6/00* (2006.01)
*A61B 6/06* (2006.01)

(52) U.S. Cl.
CPC ................ *A61B 6/463* (2013.01); *A61B 6/06* (2013.01); *A61B 6/467* (2013.01); *A61B 6/548* (2013.01)

(58) Field of Classification Search
CPC .................................. A61B 6/463; A61B 6/06
See application file for complete search history.

(56) References Cited

U.S. PATENT DOCUMENTS 6,314,310 B1 * 11/2001 Ben-Haim ............. A61B 90/36
                                                                  600/424
2005/0259116 A1 * 11/2005 Araoka .................. G16H 30/20
                                                                  345/619

(Continued)

FOREIGN PATENT DOCUMENTS

JP         7-265289      10/1995
JP       2012-075782     4/2012

(Continued)

OTHER PUBLICATIONS

Office Action dated Jan. 25, 2022 in Application No. 2018-074890.

*Primary Examiner* — David P Porta
*Assistant Examiner* — Mamadou Faye
(74) *Attorney, Agent, or Firm* — Oblon, McClelland, Maier & Neustadt, L.L.P.

(57) ABSTRACT

According to one embodiment, an X-ray diagnosis apparatus includes an X-ray tube, a diaphragm mechanism, an X-ray detector, image generating circuitry, a display, a first interface, a second interface, and processing circuitry. The processing circuitry controls the diaphragm mechanism and the X-ray tube according to the operation to the first interface so that the X-rays are radiated to a first radiation range, and controls the diaphragm mechanism and the X-ray tube according to the operation to the second interface so that the X-rays are radiated to a second radiation range. The processing circuitry controls the display so that the first display area displays the X-ray images sequentially generated according to radiation of the X-rays, in parallel with the radiation.

14 Claims, 14 Drawing Sheets

(56) References Cited

U.S. PATENT DOCUMENTS

| | | | | |
|---|---|---|---|---|
| 2013/0101084 A1* | 4/2013 | Shimizu | ............. | A61B 6/481 |
| | | | | 378/42 |
| 2013/0237810 A1* | 9/2013 | Iwai | ............. | A61B 6/06 |
| | | | | 600/424 |
| 2014/0168276 A1 | 6/2014 | Takeda | | |
| 2015/0003584 A1* | 1/2015 | Weisfield | ............. | G01T 1/2018 |
| | | | | 378/62 |
| 2018/0360342 A1* | 12/2018 | Fuimaono | ............. | A61B 18/1492 |

FOREIGN PATENT DOCUMENTS

| | | |
|---|---|---|
| JP | 2013-215275 | 10/2013 |
| JP | 2014-117306 | 6/2014 |

\* cited by examiner

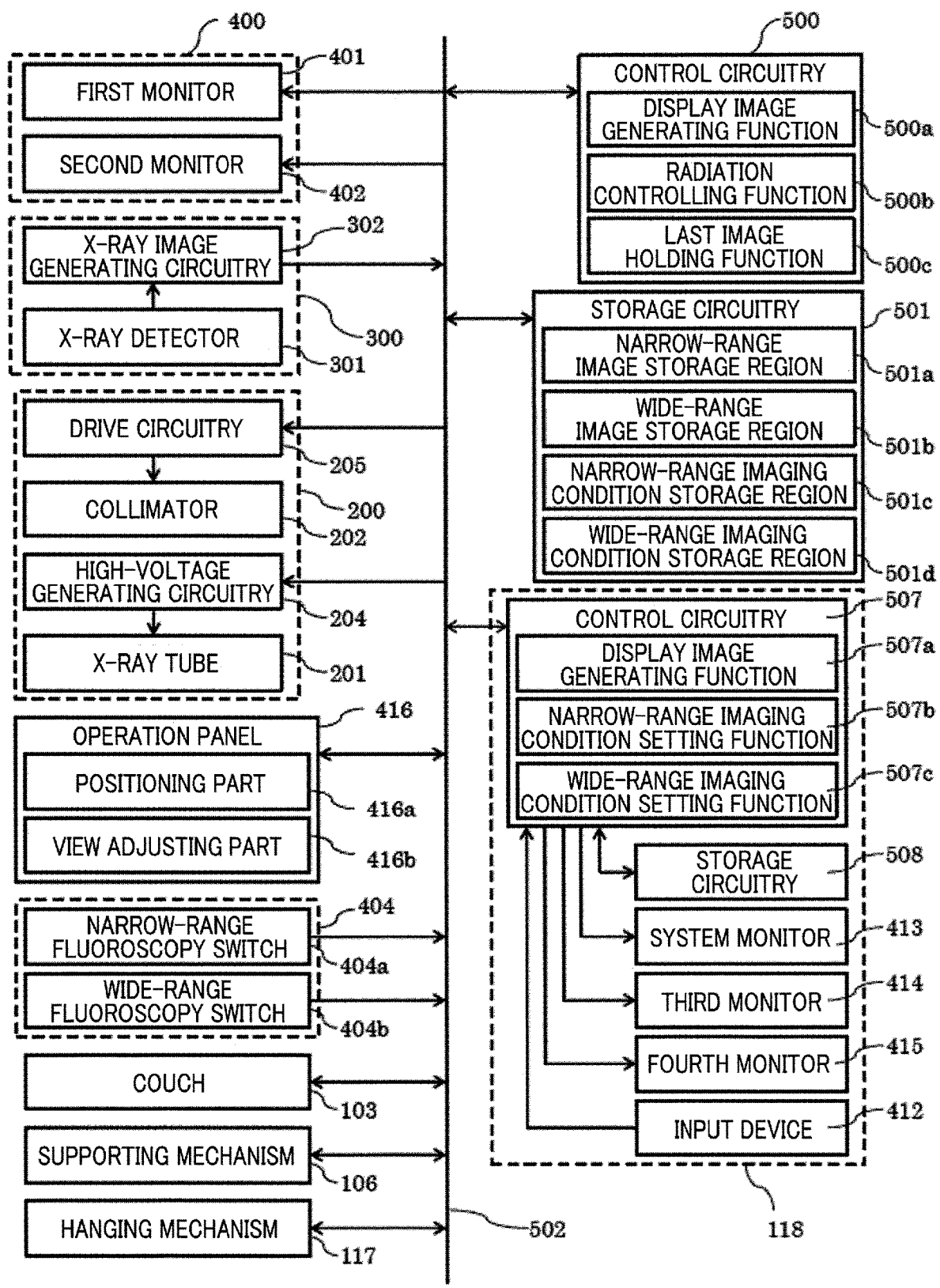
F I G. 6

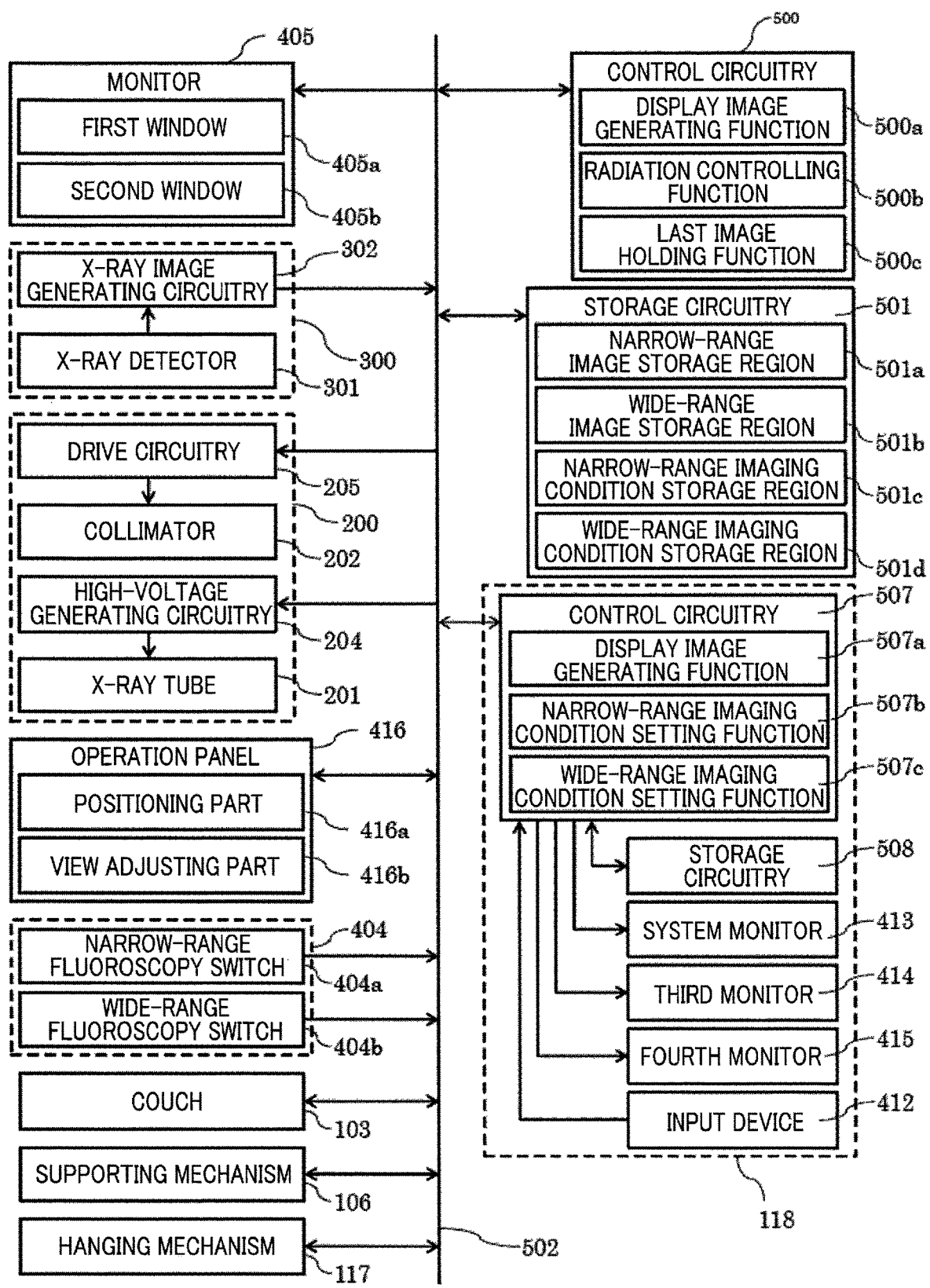
F I G. 10

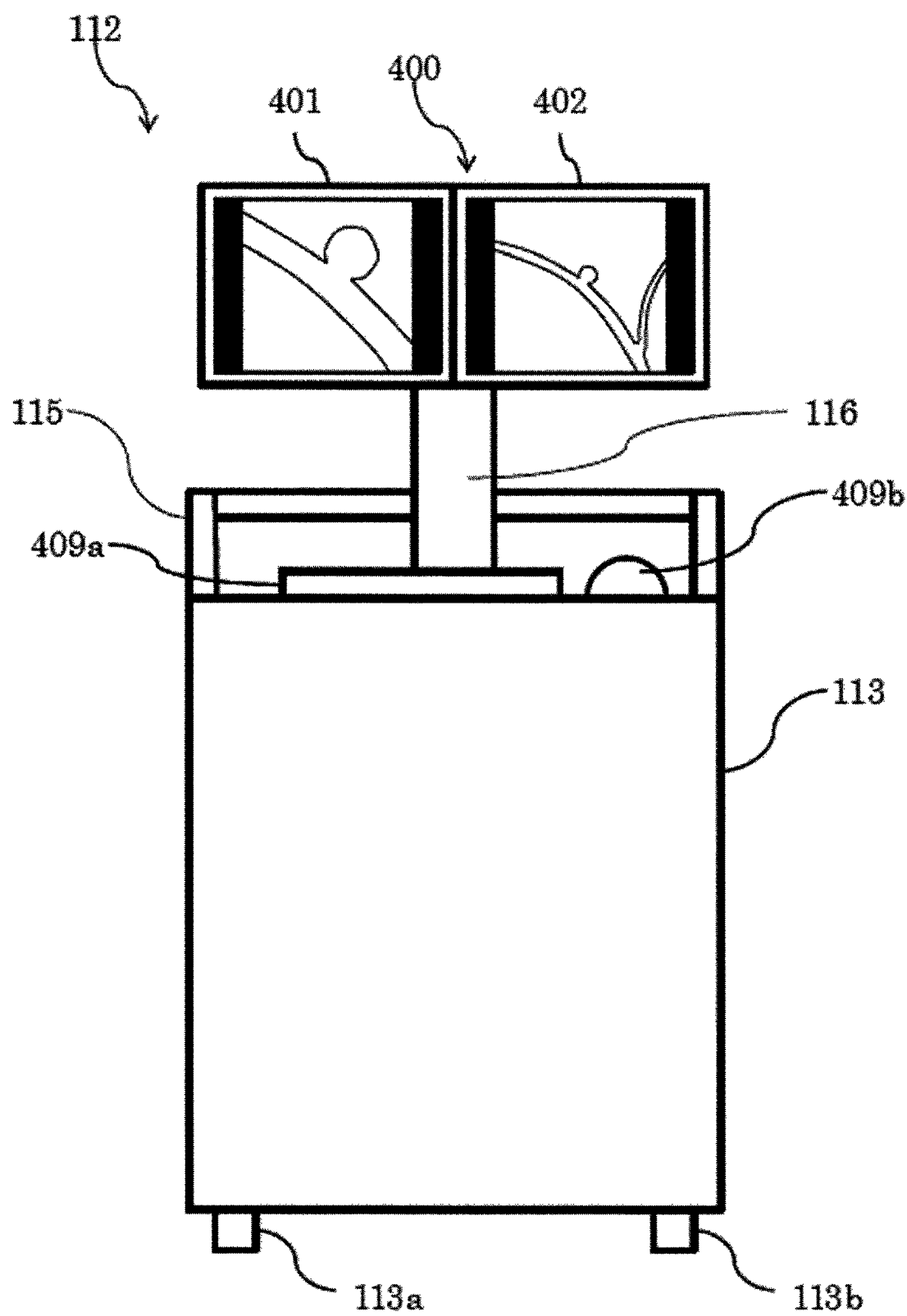
F I G. 13

X-RAY DIAGNOSIS APPARATUS

CROSS-REFERENCE TO RELATED APPLICATIONS

This application is based upon and claims the benefit of priority from prior Japanese Patent Application No. 2018-74890, filed Apr. 9, 2018, the entire contents of which are incorporated herein by reference.

FIELD

Embodiments described herein relate generally to an X-ray diagnosis apparatus.

BACKGROUND

It is often the case in treatment operations with an X-ray diagnosis apparatus that a display of an enlarged view of a subject's affected area and a display of a view covering a wide area surrounding the affected area are switchably used. In the context of such use, X-ray radiations while the display of an enlarged affected-area view is selected should be targeted at only the affected area associated with the display, so that the subject will receive a reduced dose of exposure.

However, when X-ray radiations are limited to only the affected area, images of its surrounding wide area cannot be acquired. The consequence is a failure to cope with the demand of a physician or a surgeon, or other staffs that an image of the wide area surrounding the affected area can also be referred to while an enlarged view of the affected area is displayed. There are occasions as well, where a physician or others want to refer to an enlarged image of an affected area when the physician is using a display of an image of the wide area surrounding the affected area.

Moreover, it is also desired that a treatment can be conducted with frequent switching of radiation ranges, so the related operations should be simple. In sum, there is a demand for enabling the parallel display of images in two ranges, i.e., a wide range and a narrow range, with simple operations.

BRIEF DESCRIPTION OF THE DRAWINGS

FIG. 6 is a functional block diagram showing a control system according to the first embodiment.

FIG. 10 is a functional block diagram showing a control system according to the second embodiment.

FIG. 13 is a front view of the external design of a monitor wagon device according to the third embodiment.

DETAILED DESCRIPTION

According to a certain embodiment, an X-ray diagnosis apparatus includes an X-ray tube, a diaphragm mechanism, an X-ray detector, a display, a first interface, a second interface, image generating circuitry, and processing circuitry.

The X-ray tube generates X-rays.

The diaphragm mechanism limits a radiation range of the X-rays.

The X-ray detector is provided so that it faces the X-ray tube and detects the X-rays.

The display includes a first display area and a second display area.

The first interface and the second interface receive an operation from an operator or manipulator.

The processing circuitry controls the diaphragm mechanism and the X-ray tube according to the operation to the first interface so that the X-rays are radiated to a first radiation range, and controls the diaphragm mechanism and the X-ray tube according to the operation to the second interface so that the X-rays are radiated to a second radiation range.

The image generating circuitry sequentially generates X-ray images based on X-ray detection by the X-ray detector.

The processing circuitry controls the display so that the first display area displays the X-ray images sequentially generated according to radiation of the X-rays, in parallel with the radiation of the X-rays.

In this configuration, the processing circuitry controls the display so that, in response to a switchover of the radiation range from the first radiation range to the second radiation range for further radiation of the X-rays after the radiation to the first radiation range, the first display area displays the X-ray images sequentially generated according to the further radiation to the second radiation range, in parallel with the further radiation, and the second display area displays an image based on the X-ray images having been generated according to the radiation to the first radiation range and displayed on the first display area.

Now, embodiments will be described with reference to the drawings. The description will use the same reference symbols for substantially the same components or elements across the various embodiments, and redundant explanations will be omitted.

First Embodiment

An X-ray diagnosis apparatus according to the first embodiment is intended for use in treatment operations which may mainly be an intravascular treatment and a surgical operation. First, configurations of the respective components in the X-ray diagnosis apparatus according to this embodiment will be described with reference to FIGS. 1 to 8.

Figure 1:
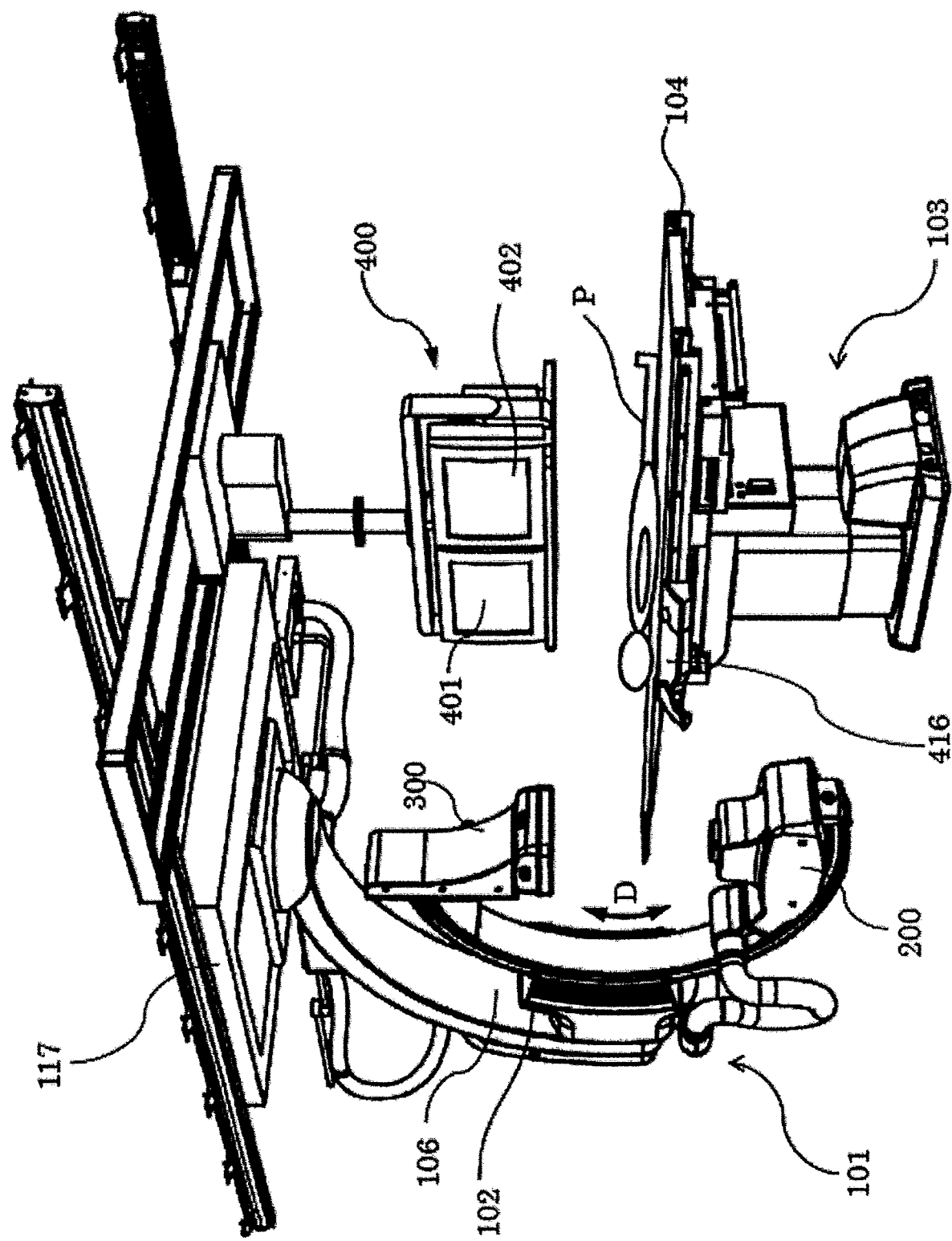
FIG. 1 is a perspective view including the external designs of a C-arm device, a couch, a display device, and a hanging mechanism that constitute an X-ray diagnosis apparatus according to a first embodiment.

As shown in FIG. 1, the X-ray diagnosis apparatus according to the embodiment includes a C-arm device 101 constituted by a C-arm 102, an X-ray generating device 200, an X-ray detecting device 300, and a supporting mechanism 106. The C-arm 102 is a C-profiled support unit for the X-ray generating device 200 to be held at one end and the X-ray detecting device 300 to be held at the other end so that the X-ray generating device 200 and the X-ray detecting device 300 face each other. The C-arm 102 is attached to a hanging mechanism 117 on the ceiling of an examination room, via the supporting mechanism 106. The hanging mechanism 117 is adapted to drive the C-arm device 101 back and forth and from side to side, and to also rotate the C-arm device 101 around a vertical axis. The supporting mechanism 106 is adapted to drive the C-arm 102 in a direction D along its arc.

Figure 2:
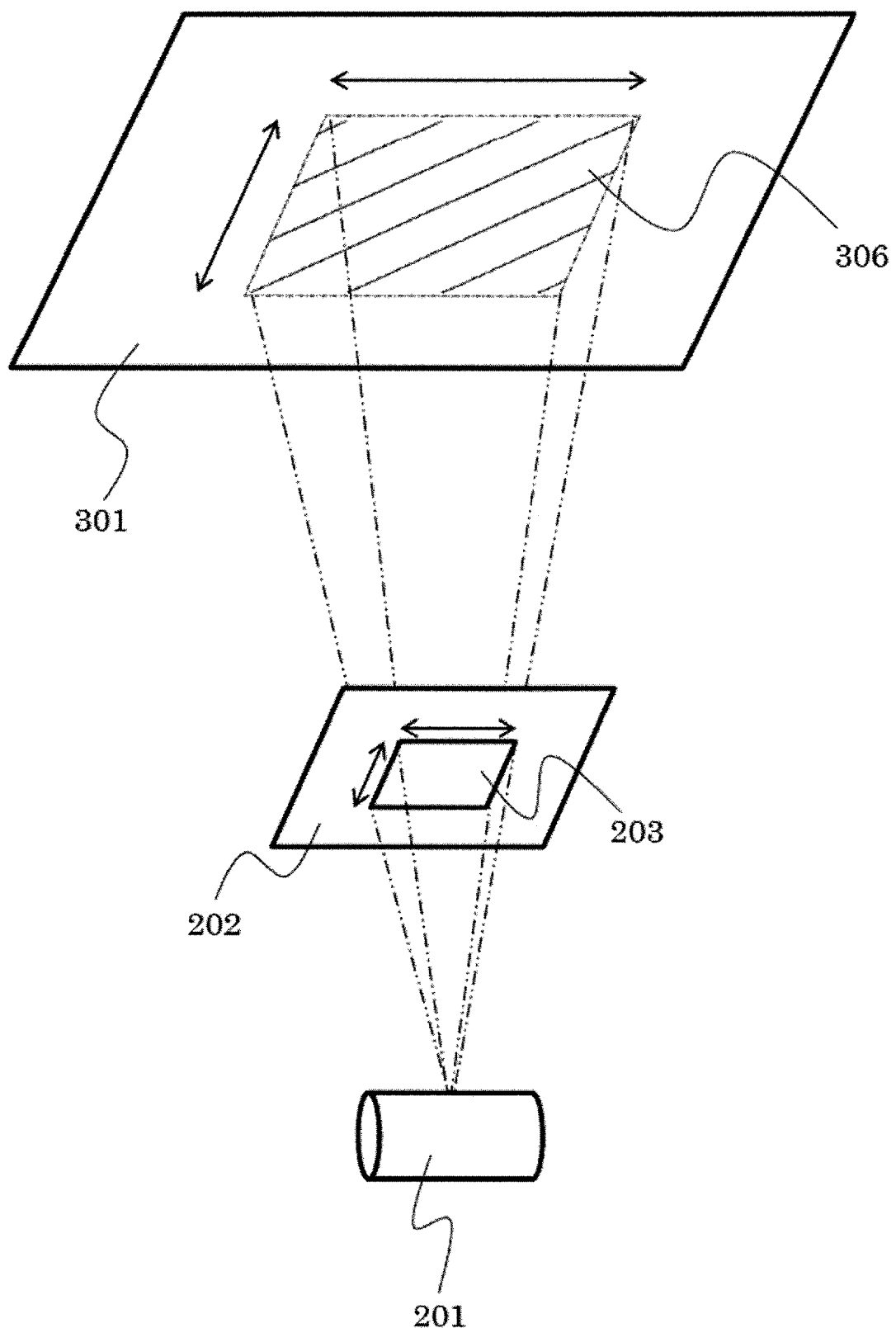
FIG. 2 is a schematic diagram including an X-ray tube, a collimator, and an X-ray detector according to the first embodiment.

The X-ray generating device 200 includes an X-ray tube 201 for generating X-rays and a collimator 202 for limiting the X-ray radiation ranges, as shown in FIG. 2. While not shown in the figure, the X-ray tube 201 is provided with filaments for generating electron beams and targets for generating X-rays upon receipt of the electron beams. The collimator 202 has a quadrilateral opening 203 which may be defined by four diaphragm blades. The collimator 202 is adapted to slide the four diaphragm blades using the application of a drive voltage from drive circuitry 205 (cf. FIG. 6) to change the shape and size of the opening 203. The X-rays coming from the targets are limited by the collimator 202, and radiated toward an X-ray detector 301 of the X-ray detecting device 300 with a shape and size according to the opening 203. That is, the X-ray detector 301 will have an irradiated region 306 of a quadrilateral shape analogous to the shape of the opening 203. The collimator 202 is one example of the "diaphragm mechanism".

Figure 3:
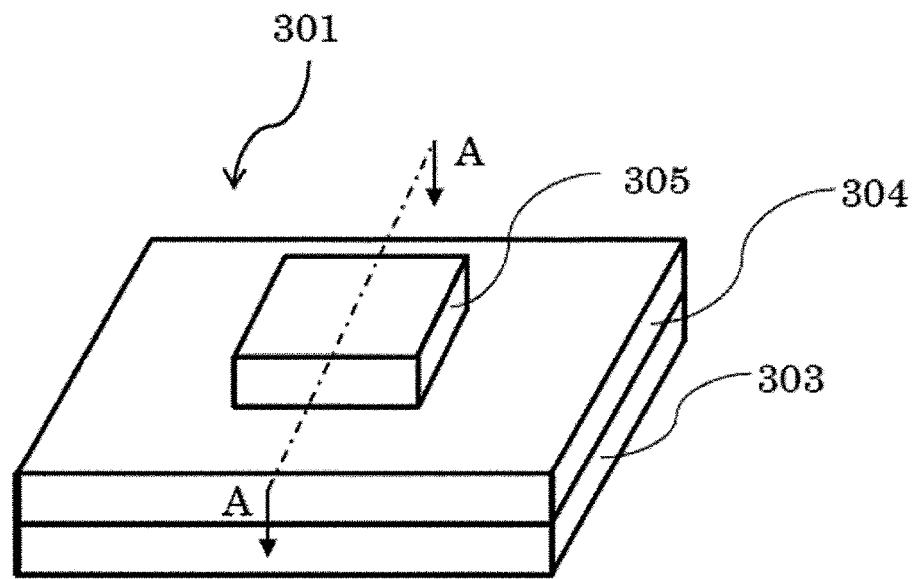
FIG. 3 is a schematic perspective view of the X-ray detector according to the first embodiment.
Figure 4:
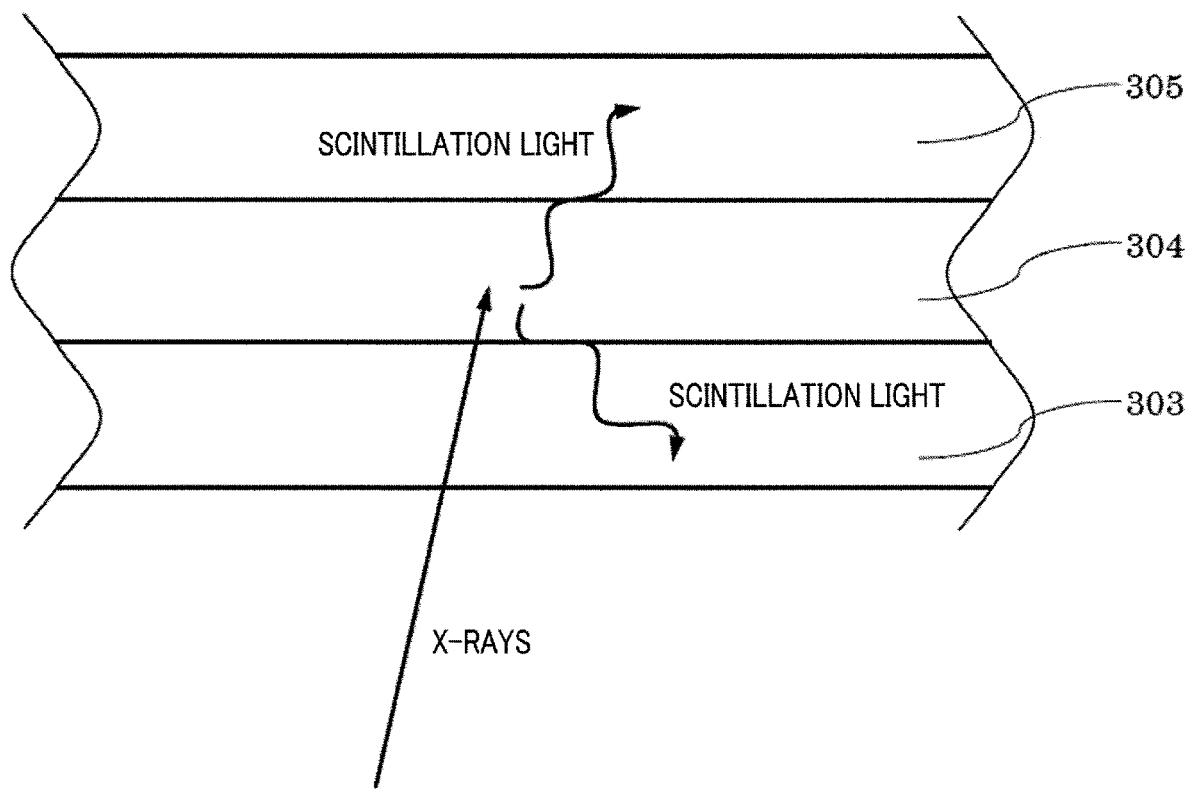
FIG. 4 is a schematic sectional view of the X-ray detector according to the first embodiment, taken along the plane A-A in FIG. 3.

The X-ray detecting device 300 includes the X-ray detector 301 and X-ray image generating circuitry 302 (cf. FIG. 6). The X-ray detector 301 is provided so that it faces the X-ray tube 201 and detects the X-rays. More specifically, the X-ray detector 301 detects the X-rays radiated from the X-ray generating device 200, and outputs electric signals based on the X-rays to the X-ray image generating circuitry 302. The X-ray image generating circuitry 302 sequentially generates X-ray images based on the outputs from the X-ray detector 301. The X-ray detector 301 has a structure including a photodiode layer 303, a photodiode layer 305, and a scintillator layer 304 disposed therebetween, as shown in FIGS. 3 and 4. The scintillator layer 304 is made of, for example, cesium iodide doped with thallium, and adapted to absorb incident X-rays and radiate a scintillation light. The photodiode layer 303 and the photodiode layer 305 are each constituted by a large number of two-dimensionally arranged photodiodes (not shown in the figures), and adapted to convert the scintillation light from the scintillator layer 304 into electric signals. The photodiode layer 303 may employ a TFT array substrate. The photodiode layer 305 may have a CMOS gate structure. In the photodiode layer 305, the photodiodes are more densely arranged as compared to the photodiodes in the photodiode layer 303.

In an imaging plane, the photodiode layer 305 is located on a center portion of the photodiode layer 303, and occupies a smaller area than the photodiode layer 303 does. In other words, the periphery of the photodiode layer 305 is located inside the periphery of the photodiode layer 305 in the imaging plane.

The X-rays from the X-ray generating device 200 are transmitted through a subject P and enter the X-ray detector 301. The X-rays are first incident on the photodiode layer 303 but pass through the photodiode layer 303, as the X-rays falling outside the detection wavelength of the photodiode layer 303. The X-rays are then incident on the scintillator layer 304, where they are converted into a scintillation light as discussed above. This scintillation light is detected by the photodiode layer 303 or the photodiode layer 305.

The X-ray detector 301, as a specific configuration, may include a high-resolution detecting part having a pixel density higher than another part of its X-ray detecting portion. Such a "high-resolution detecting part", "another part", and their embracing "X-ray detecting portion" may also be called a "high-resolution detecting layer", "another layer", and "X-ray detecting layers". It is also possible that the "another layer" is called a "low-resolution detecting layer". That is, how the components should be called may be freely and discretionarily changed, as long as there is no confusion among the components. This applies to the names of all components and elements throughout this disclosure. Note that the "X-ray detecting portion" here corresponds to the combination of two photodiode layers, i.e., the photodiode layer 303 and the photodiode layer 305. Within this portion, the "another part" corresponds to the photodiode layer 303. Also, the "high-resolution detecting part" corresponds to the photodiode layer 305. With regard to the radiation ranges to be employed, the "first radiation range" may be set to be covered by the "high-resolution detecting part". The "second radiation range" may be set to be wider or larger than the "high-resolution detecting part". Also, the first radiation range or the second radiation range may encompass the other. That is, the second radiation range may encompass the first radiation range, for example. The X-ray image generating circuitry 302 may be adapted to use the outputs from the "high-resolution detecting part", i.e., not to use the output from the "another part", to generate X-ray images (narrow-range images) in response to an operation to a narrow-range fluoroscopy switch 404a. Also, the X-ray image generating circuitry 302 may be adapted to use at least the outputs from the "another part" to generate X-ray images (wide-range images) in response to an operation to a wide-range fluoroscopy switch 404b. Note that the use of at least the outputs from the "another part" in this context means not only use of only the outputs from the "another part" but also use of both the outputs from the "another part" and the outputs from the "high-resolution detecting part". For the present embodiment, the description will mainly refer to the instances of using only the outputs from the "another part".

As discussed, photodiodes are more densely arranged in the photodiode layer 305 than in the photodiode layer 303. Accordingly, the photodiode layer 305 allows for the acquisition of images having a high resolution (images of high spatial resolution) as compared to the cases of using the photodiode layer 303 for X-ray detection. It is additionally noted that, when the photodiode layer 305 corresponds to the first radiation range and the photodiode layer 303 corresponds to the second radiation range, the X-ray images generated according to the radiations to the first radiation range have a higher spatial resolution than the X-ray images generated according to the radiations to the second radiation range. However, the X-ray detection by the photodiode layer 305 requires a subject to be irradiated with X-rays of a higher intensity than in the X-ray detection by the photodiode layer 303, since the photodiode layer 305 involves fewer incident photons for each photodiode therein, which could deteriorate the S/N ratio. In the present disclosure, the "intensity" of an X-ray is represented by the number of photons that pass through a unit area per unit time (the unit area being perpendicular to the traveling direction of light).

The X-ray detector 301 according to the embodiment has a structure in which the photodiode layer 303 and the photodiode layer 305 are stacked in the direction of X-ray radiations, but this is not a limitation. For example, the X-ray detector 301 may arrange the photodiode layer 303 and the photodiode layer 305 to be on the same plane. In this arrangement, the photodiode layer 303 does not overlap the region where the photodiode layer 305 is provided. As such, in order to image a range that is larger than the detection range of the photodiode layer 305, both the photodiode layer 303 and the photodiode layer 305 are used. This instance corresponds to the use of at least the outputs from the "another part" being the use of both the outputs from the "another part" and the outputs from the "high-resolution detecting part", as discussed above. At this time, a proper S/N ratio can be secured by collecting up the outputs of some of the photodiodes constituting the photodiode layer 305. This contributes to the reduction in dose of exposure of the subject.

Turning back to FIG. 1, the X-ray diagnosis apparatus according to the embodiment includes a display device 400. The display device 400 includes two monitors, i.e., a first monitor 401 and a second monitor 402, and can provide displays of different still images or moving images through these monitors. As a matter of course, it can display the same still image or moving image on the first monitor 401 and the second monitor 402. The display screen of the first monitor 401 may function as the "first display area", and the display screen of the second monitor 402 may function as the "second display area". In this embodiment, the display device 400 including the first monitor 401 and the second monitor 402 functions as the "display", but the first monitor 401 and the second monitor 402 may be disposed at the locations separate from each other. The function of the "display" can also be realized by the combination of the first monitor 401 and the second monitor 402 located away from each other.

The X-ray diagnosis apparatus according to the embodiment further includes a couch 103. The couch 103 has a couch top 104 for the placement of the subject P thereon. The couch 103 can move the couch top 104 in triaxial directions including the height direction, the lengthwise direction, and the transverse direction, so that the subject P can be brought to any position suitable for treatment and imaging. For imaging operations, the couch top 104 and the C-arm 102 are moved so that the affected area of the subject P is located between the X-ray generating device 200 and the X-ray detecting device 300. In this manner, images of the affected area and its surrounding area of the subject P can be acquired.

The couch 103 is provided with an operation panel 416 as shown in FIG. 1. This operation panel 416 includes a positioning part 416a and a view adjusting part 416b (cf. FIG. 6). The positioning part 416a is for operating the hanging mechanism 117, the supporting mechanism 106, and the couch 103. Inputs to the positioning part 416a are referred to by control circuitry 500 which then controls the hanging mechanism 117, the supporting mechanism 106, and the couch 103 for driving. The view adjusting part 416b is for setting radiation ranges. Inputs to the view adjusting part 416b are referred to by the control circuitry 500 which then sends control signals for the collimator 202 to the drive circuitry 205.

Figure 5:
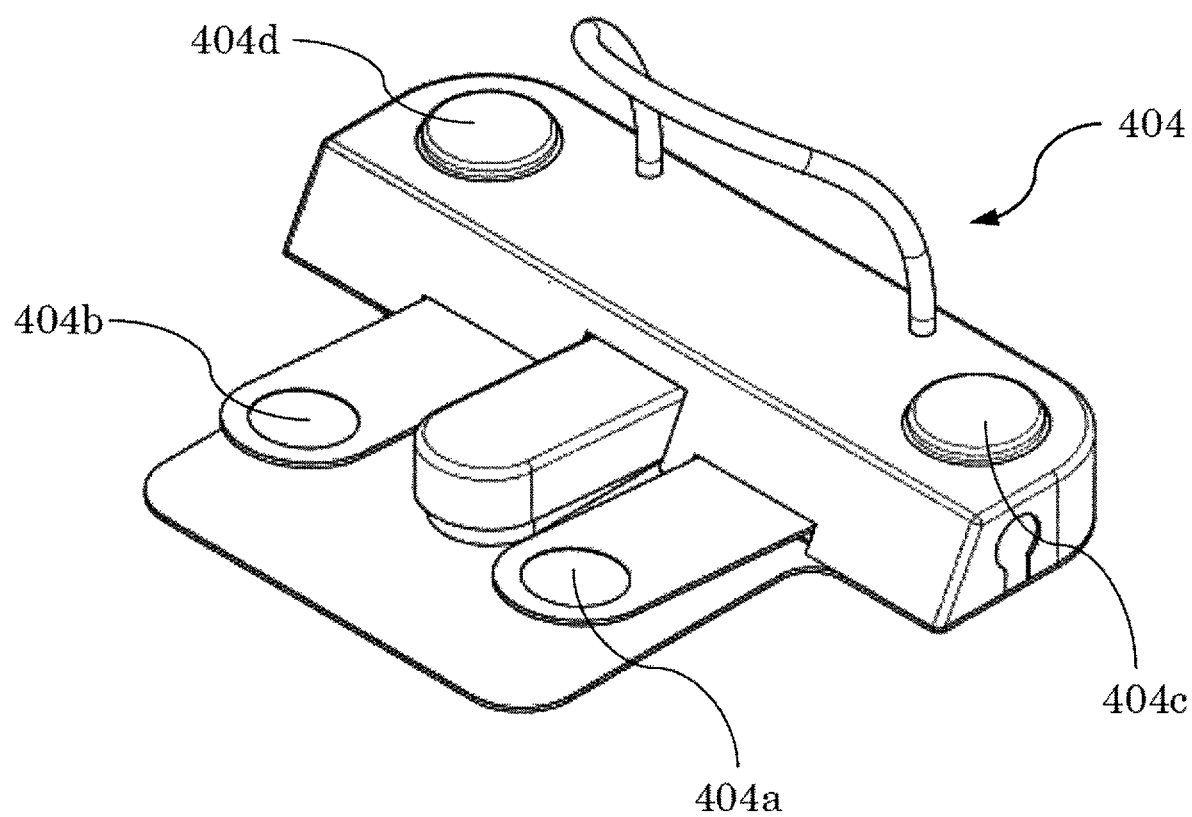
FIG. 5 is a perspective view of the external design of a foot switch device according to the first embodiment.

The X-ray diagnosis apparatus according to the embodiment includes a foot switch device 404 as shown in FIG. 5. The foot switch device 404 is provided at the foot of a physician, and adapted to be stepped on by the physician's foot for operation. The foot switch device 404 includes the aforementioned narrow-range fluoroscopy switch 404a and wide-range fluoroscopy switch 404b, as well as a sub-switch 404c and a sub-switch 404d. For operation, stepping on the narrow-range fluoroscopy switch 404a turns on the fluoroscopy that uses the dense photodiode layer 305 with the opening 203 of the collimator 202 narrowed down, that is, with a small radiation range. Also, stepping on the wide-range fluoroscopy switch 404b turns on the fluoroscopy that uses the coarse photodiode layer 303 with the opening 203 of the collimator 202 widened, that is, with a large radiation range. These operations will be described in more detail later. The sub-switch 404c and the sub-switch 404d can be assigned a variety of functions in advance via a console 118, for facilitating physician-friendliness. The narrow-range fluoroscopy switch 404a and the wide-range fluoroscopy switch 404b are respective examples of the "first interface" and the "second interface" for receiving operational inputs from its operator or manipulator.

A control system according to the present embodiment will be described with reference to FIG. 6. The X-ray diagnosis apparatus according to this embodiment includes the console 118, the control circuitry 500, and storage circuitry 501, in addition to the components described above, such as the X-ray generating device 200, the X-ray detecting device 300, the display device 400, etc. Each of these components is connected with a bus 502 so as to be communicable with other components via the bus 502. Note that the control system according to the embodiment assumes use of the bus 502 which is a single member for making connections among the components. The component connections may instead or additionally be made in various forms of topology including, for example, network connections, hub connections, and so on.

The console 118 is furnished in an operation room separate from the examination room where the C-arm device 101, the display device 400, etc., are provided. The console 118 is used for operations to set imaging conditions, operations for image processing, operations for devices in the examination room, operations for file management, and so on. The console 118 includes control circuitry 507, storage circuitry 508, a system monitor 413, a third monitor 414, a fourth monitor 415, an input device 412, etc.

The control circuitry 507 has a display image generating function 507a for generating images to be displayed on the system monitor 413, the third monitor 414, and the fourth monitor 415.

The control circuitry 507 also has a narrow-range imaging condition setting function 507b and a wide-range imaging condition setting function 507c. With the narrow-range imaging condition setting function 507b, the control circuitry 507 sets the imaging conditions for the imaging operation that uses the dense photodiode layer 305 with the size of the radiation range narrowed down. Data of the imaging conditions set by the narrow-range imaging condition setting function 507b is stored in a narrow-range imaging condition storage region 501c of the storage circuitry 501. Also, the control circuitry 507, with the wide-range imaging condition setting function 507c, sets the imaging conditions for the imaging operation that uses the coarse photodiode layer 303 with the size of the radiation range widened. Data of the imaging conditions set by the wide-range imaging condition setting function 507c is stored in a wide-range imaging condition storage region 501d of the storage circuitry 501.

The system monitor 413 is adapted to display the imaging conditions, information about stored files, information about the subject, etc. The third monitor 414 and the fourth monitor 415 will be described later.

The input device 412 is constituted by a keyboard, a mouse, and the like (now shown). The input device 412 allows for the manipulation of GUIs displayed on the system monitor 413 so that change of the imaging conditions, read and save of files, entry and change of subject information, and other operations can be performed.

The console 118, including the control circuitry 507 with the narrow-range imaging condition setting function 507b, functions as a narrow-range imaging condition setting unit for setting the imaging conditions based on the inputs to the input device 412, for performing the X-ray radiations with the opening 203 narrowed down, that is, with a small radiation range. Also, the console 118, including the control circuitry 507 with the wide-range imaging condition setting function 507c, functions as a wide-range imaging condition setting unit for setting the imaging conditions based on the inputs to the input device 412, for performing the X-ray radiations with the opening 203 widened, that is, with a large radiation range.

The storage circuitry 508 is a memory for storing information items such as information about the display setting for the system monitor 413, the third monitor 414, and the fourth monitor 415.

The control circuitry 500 is a processor that takes various controls in the control system of the X-ray diagnosis apparatus according to the present embodiment. The control circuitry 500, in particular, has a display image generating function 500a, a radiation controlling function 500b, and a last image holding function 500c. With the display image generating function 500a, the control circuitry 500 generates images to be displayed on the first monitor 401 or the second monitor 402, based on image data received from the X-ray detecting device 300, the storage circuitry 501, etc. With the radiation controlling function 500b, the control circuitry 500 controls the X-ray generating device 200 based on the inputs from the operation panel 416, the foot switch device 404, etc. The last image holding function 500c will be described later. The control circuitry 500 is one example of the "processing circuitry".

The storage circuitry 501 is a memory for storing data items such as the image data acquired by the X-ray detecting device 300, data about the setting of the imaging conditions, and data about the display setting for the display device 400.

The control circuitry 500 calculates parameters under each of the imaging conditions, such as the shape and size of the opening 203 of the collimator 202, and the tube current and tube voltage of the X-ray tube 201, based on the input signals from the control circuitry 507 of the console 118. The control circuitry 500 stores data of the calculated parameters in the narrow-range imaging condition storage region 501c or the wide-range imaging condition storage region 501d in the storage circuitry 501. The control circuitry 500 also reads the data of the various parameters for the imaging conditions from the narrow-range imaging condition storage region 501c or the wide-range imaging condition storage region 501d in the storage circuitry 501, based on the input signals from the foot switch device 404. Based on the read data, the control circuitry 500 then outputs control signals to the drive circuitry 205 of the collimator 202, as well as to high-voltage generating circuitry 204 of the X-ray generating device 200. In other words, the control circuitry 500 controls the collimator 202 and the X-ray tube 201 according to the operational inputs to the narrow-range fluoroscopy switch 404a so that the X-rays are radiated to the first radiation range, and controls the collimator 202 and the X-ray tube 201 according to the operational inputs to the wide-range fluoroscopy switch 404b so that the X-rays are radiated to the second radiation range. Controlling the X-ray tube 201 may include setting the X-rays for the first radiation range (narrow range) at an intensity higher than the X-rays for the second radiation range (wide range). Similarly, controlling the X-ray tube 201 may include setting the X-rays for the second radiation range (wide range) at an intensity lower than the X-rays for the first radiation range (narrow range).

As discussed above, X-rays, upon incident on the X-ray detecting device 300, are detected and converted into electric signals by the X-ray detector 301. The X-ray image generating circuitry 302 processes the electric signals and outputs them as image data.

Under the control of the control circuitry 500, the output image data is stored in a narrow-range image storage region 501a or a wide-range image storage region 501b, and also subjected to the image processing by the display image generating function 500a of the control circuitry 500 so as to be displayed in real time (noted as "RT display" in the drawings) on the first monitor 401. When the image data corresponds to a narrow-range image, the image data is stored in the narrow-range image storage region 501a of the storage circuitry 501. When the image data corresponds to a wide-range image, the image data is stored in the wide-range image storage region 501b of the storage circuitry 501. In either case, the control circuitry 500 causes the first monitor 401 to display the X-ray images sequentially generated according to the X-ray radiations, in parallel with the ongoing X-ray radiations.

Note that the real-time display in the context of the present disclosure does not have to be an operation to display an object strictly simultaneously with its imaging. The real-time display may be a motion display operation with a certain degree of instantaneousness that permits a physician to check the progress of the treatment currently performed by itself.

Also note that the narrow-range image storage region 501a, the wide-range image storage region 501b, the narrow-range imaging condition storage region 501c, and the wide-range imaging condition storage region 501d may be implemented by a single storage component or different storage components within the storage circuitry 501. If these storage regions are implemented by a single storage component, they may be defined by partitions there, or they may be transitory within the same zone. Each of the storage regions may also be a region which shifts around within the storage circuitry 501 according to garbage collection operations, etc. Moreover, these storage regions may be partially or entirely arranged in the storage circuitry of another device, for example, the storage circuitry 508 of the console 118.

The control circuitry 500 has the last image holding (LIH) function 500c as mentioned above. The last image holding function 500c is a function which, when X-ray radiations are stopped, keeps the display of a still image that has been acquired immediately before the stop of the radiations. The image to be displayed on the second monitor 402 may be a still image that has been generated most recently among the X-ray images generated according to the preceding radiations. During the X-ray radiations, the image data is continuously output from the X-ray image generating circuitry 302, and the images based on this image data are displayed on the first monitor 401 in real time. Once the X-ray radiations are stopped, the image data is no longer output from the X-ray image generating circuitry 302. At this time, the control circuitry 500 reads the most recent image data from the narrow-range image storage region 501a or the wide-range image storage region 501b of the storage circuitry 501, and causes the first monitor 401 to display the image based on this most recent image data. In this manner, the display on the first monitor 401 can be kept in the state before the stop of the X-ray radiations.

The description will use the term "narrow-range image" to indicate an image acquired when the size of the radiation range is set to be small. The term "wide-range image" will be used to indicate an image acquired when the size of the radiation range is set to be larger than the radiation range for the narrow-range images. Also in the following description, the most recent image among the images acquired with the small radiation range will be called "last image from the narrow-range imaging". The most recent image among the images acquired with the radiation range larger than the radiation range for the narrow-range images will be called "last image from the wide-range imaging".

Now, the flow of control for performing fluoroscopy imaging will be described. In advance of initiating the fluoroscopy imaging, the imaging conditions for acquiring narrow-range images and the imaging conditions for acquiring wide-range images are set via the console 118. Upon setting the imaging conditions for the both, a fluoroscopy mode for accepting operations for the fluoroscopy imaging starts. The fluoroscopy mode involves the control constituted by steps S1 to S22 shown in the flowchart of FIGS. 7A and 7B.

Upon start of the fluoroscopy mode (S1), the control circuitry 500 first determines whether or not an exit operation has been performed. Upon determining the absence of the exit operation (No in S2), the control circuitry 500 determines whether or not the first monitor 401 is in the state of holding the last image from the narrow-range imaging (S3).

If it is determined that the first monitor 401 is in the state of holding the last image from the narrow-range imaging (Yes in S3), the control circuitry 500 determines whether or not the narrow-range fluoroscopy switch 404a of the foot switch device 404 is turned on (S4). Upon determining that the narrow-range fluoroscopy switch 404a is turned on (Yes in S4), the control circuitry 500 causes the first monitor 401 to perform the real-time display of the narrow-range images while permitting the X-ray radiations to continue (S5), and maintains the real-time display operations for the narrow-range images as long as the narrow-range fluoroscopy switch 404a is on (Yes in S6). At this time, the data output from the X-ray image generating circuitry 302 is stored in the narrow-range image storage region 501a as discussed above, in such a manner that the incoming new data continuously overwrites the stored data. When the narrow-range fluoroscopy switch 404a is turned off (No in S6), the real-time display is terminated, and the control circuitry 500 with the above-described last image holding function 500c keeps the first monitor 401 displaying the last image from the narrow-range imaging (S7). The control flow then returns to the determination step S2.

If it is determined in step S4 that the narrow-range fluoroscopy switch 404a is not on (No in S4), the control circuitry 500 determines whether or not the wide-range fluoroscopy switch 404b is turned on (S8). Upon determining that the wide-range fluoroscopy switch 404b is turned on (Yes in S8), the control circuitry 500 causes the second monitor 402 to display the last image from the narrow-range imaging which is stored in the narrow-range image storage region 501a, that is, to display the image having been displayed on the first monitor 401 (S9), and causes the first monitor 401 to display the wide-range images in real time (S10). In other words, the control circuitry 500, in response to a switchover of the radiation range from the first radiation range to the second radiation range for performing further radiations after the radiations to the first radiation range (Yes in S8), causes the first monitor 401 to display the X-ray images sequentially generated according to these further radiations to the second radiation range, in parallel with the further radiations (S10), while causing the second monitor 402 to display the image based on the X-ray images having been generated according to the preceding X-ray radiations to the first radiation range and displayed on the first display area (S9). At this time, the data output from the X-ray image generating circuitry 302 is stored in the wide-range image storage region 501b as discussed above, in such a manner that the incoming new data continuously overwrites the stored data. The control circuitry 500 maintains the real-time display operations for the wide-range images as long as the wide-range fluoroscopy switch 404b is on (Yes in S11). When the wide-range fluoroscopy switch 404b is turned off (No in S11), the control circuitry 500 with the above-described last image holding function 500c keeps the first monitor 401 displaying the last image from the wide-range imaging (S12). The control flow then returns to the determination step S2.

If it is determined in step S8 that the wide-range fluoroscopy switch 404b is not on (No in S8), the control circuitry 500 returns to step S2 for exit determination, without changing the display on either of the first monitor 401 and the second monitor 402.

In step S3, if it is determined that the first monitor 401 is not in the state of holding the last image from the narrow-range imaging (No in S3), the control circuitry 500 determines whether or not the wide-range fluoroscopy switch 404b is turned on (S13). Upon determining that the wide-range fluoroscopy switch 404b is turned on (Yes in S13), the control circuitry 500 performs control similar to steps S5 to S7, but with the narrow-range images replaced by the wide-range images (S14 to S16). Specifically, the control circuitry 500 causes the first monitor 401 to display the wide-range images in real time, for the period during which the wide-range fluoroscopy switch 404b is on (S14, and Yes in S15). When the wide-range fluoroscopy switch 404b is turned off (No in S15), the control circuitry 500 holds the display of the last image from the wide-range imaging, on the first monitor 401 (S16). The control flow then returns to the determination step S2.

Upon determining that the wide-range fluoroscopy switch 404b is not on (No in S13), the control circuitry 500 performs control similar to steps S8 to S12, but with the narrow-range images replaced by the wide-range images (S17 to S21). Specifically, if it is determined that the narrow-range fluoroscopy switch 404a is turned on (Yes in S17), the control circuitry 500 holds the display of the last image from the wide-range imaging, on the second monitor 402 (S18). Together, the control circuitry 500 causes the first monitor 401 to display the narrow-range images in real time, for the period during which the narrow-range fluoroscopy switch 404a is on (S19, and Yes in S20). In other words, when performing the radiations to the first radiation range after the radiations to the second radiation range (Yes in S17), the control circuitry 500 controls the display device 400 so that the first monitor 401 sequentially displays the X-ray images generated according to the radiations to the first radiation range (S19, and Yes in S20) and that the second monitor 402 displays the image based on the X-ray images having been generated according to the preceding X-ray radiations to the second radiation range and displayed on the first monitor 401 (S18). Then, when the narrow-range fluoroscopy switch 404a is turned off (No in S20), the control circuitry 500 holds the display of the last image from the wide-range imaging, on the first monitor 401 (S21). The control flow then returns to the determination step S2. If it is determined that the narrow-range fluoroscopy switch 404a is not on (No in S17), the control circuitry 500 returns to step S2, without changing the display on either of the first monitor 401 and the second monitor 402. In the instance where the first monitor 401 is not in the state of displaying the wide-range image at the time of step S18, that is, when the wide-range image storage region 501b stores no last image from the wide-range imaging, the second monitor 402 does not have to display an image.

If it is determined in step S2 that the exit operation is performed (Yes in S2), the fluoroscopy mode comes to the end (S22).

How the displays on the first monitor 401 and the second monitor 402 would concretely change in the process of the above control flow will be described with reference to FIGS. 7A, 7B, and 8. The description will assume a starting condition where a display of the last image from the narrow-range imaging is held on the first monitor 401, and a display of the last image from the wide-range imaging is held on the second monitor 402. Now, a physician will step on the wide-range fluoroscopy switch 404b, and subsequently on the narrow-range fluoroscopy switch 404a.

While the display of the last image from the narrow-range imaging is held on the first monitor 401, a processing routine of tracking [No in S2], [Yes in S3], [No in S4], and [No in S8] is repeated until the wide-range fluoroscopy switch 404b is stepped on. In this condition, once the wide-range fluoroscopy switch 404b is stepped on, the process advances to step S9 instead of returning to step S2 (Yes in S8), as discussed above. Then, the second monitor 402 is caused to hold the display of the last image from the narrow-range imaging (S9), and the first monitor 401 is caused to start displaying the wide-range images in real time (S10), as discussed.

Figure 8:
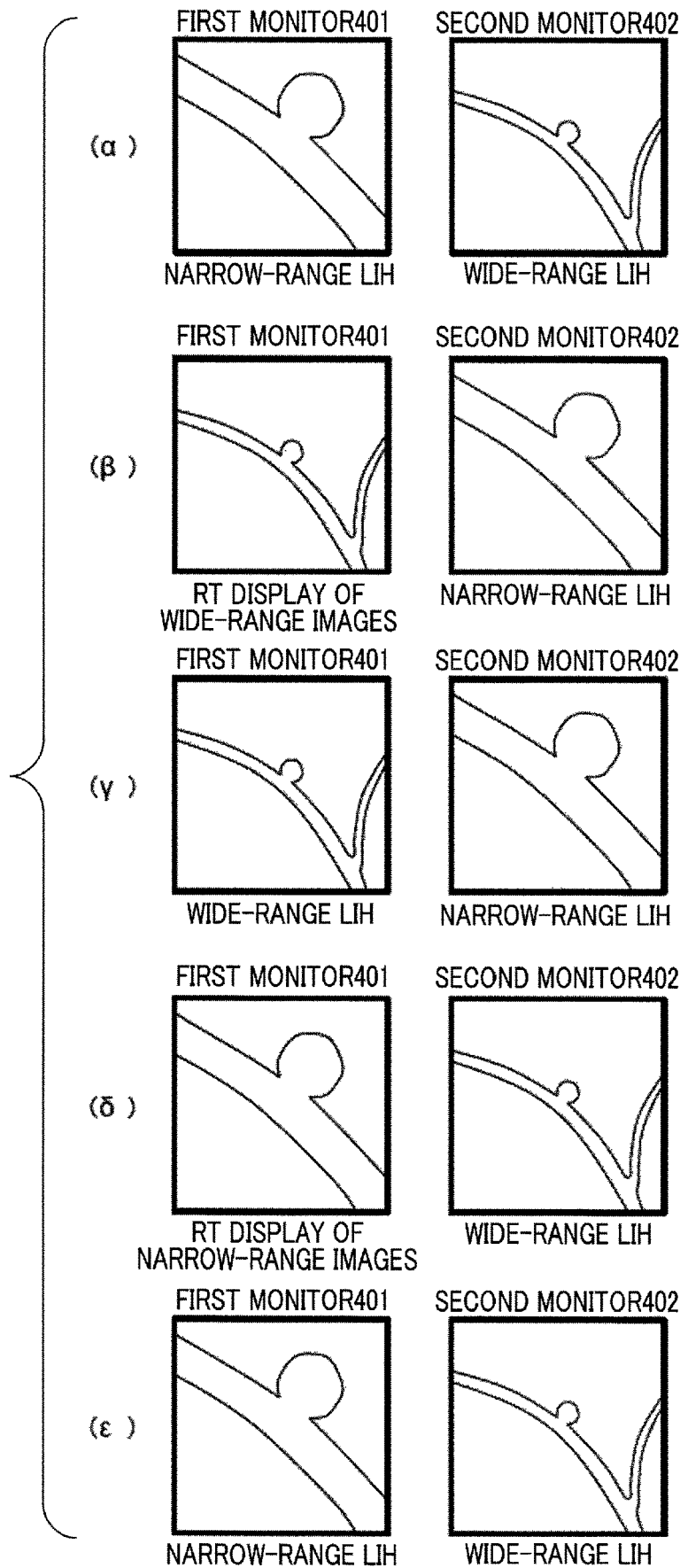
FIG. 8 is a diagram showing display switchover actions of a first monitor and a second monitor according to the first embodiment.

At this time, the displays on the first monitor 401 and the second monitor 402 change as shown in FIG. 8, from (α) to (β). Before stepping on of the wide-range fluoroscopy switch 404b, the first monitor 401 displays the last image from the narrow-range imaging and the second monitor 402 displays the last image from the wide-range imaging, as shown in FIG. 8 (α). Upon stepping on of the wide-range fluoroscopy switch 404b, the first monitor 401 performs the real-time display of the wide-range images and the second monitor 402 displays the last image from the narrow-range imaging that has been displayed on the first monitor 401 by then, as shown in FIG. 8 (β).

If the physician quits stepping on the wide-range fluoroscopy switch 404b, the process advances from step S11 to step S12 (No in S11), and the first monitor 401 is caused to hold the display of the last image from the wide-range imaging (S12).

At this time, the displays on the first monitor 401 and the second monitor 402 change as shown in FIG. 8, from (β) to (γ). That is, the second monitor 402 is kept displaying the last image from the narrow-range imaging, and the first monitor 401 is caused to display the last image from the wide-range imaging in substitution for the real-time display of the wide-range images. Note that the first monitor 401 and the second monitor 402 here are both in the last-image holding state, but the last image from the wide-range imaging (held on the first monitor 401) is an image which has been acquired more recently than the last image from the narrow-range imaging (held on the second monitor 402).

After the physician quits stepping on the wide-range fluoroscopy switch 404b, the first monitor holds the display of the wide-range image, not the narrow-range image (No in S3). As such, a processing routine of tracking [No in S2], [No in S3], [No in S13], and [No in S17] is repeated until the narrow-range fluoroscopy switch 404a is stepped on. When the narrow-range fluoroscopy switch 401a is stepped on, the process advances to step S18, instead of returning to step S2 from step S17 (Yes in S17), as discussed above. Then, the second monitor 402 is caused to hold the display of the last image from the wide-range imaging (S18), and the first monitor 401 is caused to start displaying the narrow-range images in real time (S19), as discussed.

At this time, the displays on the first monitor 401 and the second monitor 402 change as shown in FIG. 8, from (γ) to (δ). That is, before stepping on of the narrow-range fluoroscopy switch 404a, the first monitor 401 displays the last image from the wide-range imaging and the second monitor 402 displays the last image from the narrow-range imaging, as shown in FIG. 8 (γ) and as described above. Upon stepping on of the narrow-range fluoroscopy switch 404a, the first monitor 401 performs the real-time display of the narrow-range images and the second monitor 402 displays the last image from the wide-range imaging that has been displayed on the first monitor 401 by then, as shown in FIG. 8 (δ).

When the physician quits stepping on the narrow-range fluoroscopy switch 404a, the process advances from step S20 to step S21 (No in S20), and the first monitor 401 is caused to hold the display of the last image from the narrow-range imaging (S21).

At this time, the displays on the first monitor 401 and the second monitor 402 change as shown in FIG. 8, from (δ) to (ε). That is, the second monitor 402 is kept holding the last image from the wide-range imaging, and the first monitor 401 is caused to hold the last image from the narrow-range imaging in substitution for the real-time display of the narrow-range images. The first monitor 401 and the second monitor 402 here are both in the last-image holding state. The last image from the narrow-range imaging, held on the first monitor 401, is an image having been acquired after the last image from the wide-range imaging, held on the second monitor 402.

Normally, the foot switch device 404 is manipulated by a physician. Staffs or the like in the examination room, other than the physician, recognize the progress of the ongoing treatment via the displays on the display device 400. If, for example, the first monitor 401 is adapted as a display area used exclusively for the narrow-range images and the second monitor 402 is adapted as a display area used exclusively for the wide-range images, no one but the physician can tell, at a glance, which of the first monitor 401 and the second monitor 402 is displaying a more recent image. According to the control shown in FIGS. 7A and 7B, the first monitor 401 displays images which are newer than the images displayed on the second monitor 402, no matter whether the X-ray radiations are being performed or halted.

This enables the staffs or the like in the examination room, other than the physician, to know the progress of the treatment at a glance.

The third monitor 414 and the fourth monitor 415 are adapted to display the respective latest images in the narrow-range imaging and the wide-range imaging, irrespective of the switchover actions for X-ray radiations. More specifically, during the X-ray radiations to the narrow range, the third monitor 414 displays the narrow-range images in real time, and the fourth monitor 415 holds the display of the last image from the wide-range imaging. During the X-ray radiations to the wide range, the third monitor 414 holds the display of the last image from the narrow-range imaging, and the fourth monitor 415 displays the wide-range images in real time. For the period of halt of the X-ray radiations, the third monitor 414 holds the display of the last image from the narrow-range imaging, and the fourth monitor 415 holds the display of the last image from the wide-range imaging. Furthermore, the third monitor 414 and the fourth monitor 415 are each adapted so that the last image is displayed with an indication of a time stamp or a time elapsed since the start of the treatment, and that the real-time moving images are displayed with an indication of the real-time display. Additionally, the third monitor 414 and the fourth monitor 415 are equipped on the console 118 in the operation room separate from the examination room where the C-arm device 101, the display device 400, etc., are provided. Also, the third monitor 414 and the fourth monitor 415 are intended for use by an operator or manipulator in the operation room separate from the examination room, and therefore, their displays are controlled differently from the display device 400 in the examination room. That is, the third monitor 414 and the fourth monitor 415 are not adapted to switch the displayed images, in order for the operator or the like in the operation room to easily recognize the progress of the treatment.

The X-ray diagnosis apparatus according to the present embodiment copes with the cases of switching the X-ray radiation ranges such that the last image acquired from the radiation range up to the switchover is kept displayed after the switchover. With this configuration, the X-ray diagnosis apparatus can present substantially fresh images based on two radiation ranges, i.e., the wide radiation range and the narrow radiation range, while achieving the reduction in dose of exposure of a subject.

This advantage is particularly prominent when the X-ray detecting device includes two types of photodiodes (high-resolution photodiodes and low-resolution photodiodes) as in the embodiment. The X-ray detecting device 300 according to the embodiment includes the low-resolution photodiode layer 303 of a wide detection range, and the high-resolution photodiode layer 305 of a range corresponding to a part of the detection range of the photodiode layer 303. When imaging operations are performed using the photodiode layer 305, the X-rays need to adopt high intensity for securing a sufficient S/N ratio, and as such, there is an extra demand for the imaging operations that the radiation range should be limited to the detection range of the photodiode layer 305 from the viewpoint of reducing the exposure dose of the subject. However, the imaging operations with such a limited radiation range cannot provide wide-area images from the photodiode layer 303. According to the embodiment, the X-ray diagnosis apparatus automatically causes, in response to an operation of limiting the radiation range to the narrow detection range of the photodiode layer 305, the second monitor 402 to hold the display of the last image from the photodiode layer 303 which has been acquired before limiting the radiation range. Therefore, the X-ray diagnosis apparatus allows for the constant check of the relatively fresh wide-area images even during the imaging operations with the limited radiation range, and consequently, the X-ray diagnosis apparatus can let the treatment operations smoothly proceed while realizing a reduced exposure dose. That is, according to the embodiment, the X-ray diagnosis apparatus always employs the X-ray intensity necessary for the latest one of the wide radiation range (low resolution) and the narrow radiation range (high resolution), and therefore, the parallel display of the wide-range image and the narrow-range image can be realized together with a reduced exposure dose.

Moreover, in the X-ray diagnosis apparatus according to the embodiment, the radiation range for the display on the first monitor 401 and the radiation range for the display on the second monitor 402 are interchanged at the time of switchover of the radiation ranges for further X-ray radiations. Accordingly, the images displayed on the first monitor 401 are always fresher than the images displayed on the second monitor 402. This configuration enables the physician to continue treatment operations without the necessity of moving its gaze away from the first monitor 401, and also allows the staffs, etc., other than the physician, to recognize the progress of the treatment at a glance. Also, the second monitor 402 is automatically caused to display the image acquired immediately before the view switchover so that this relatively new displayed image may be used as a reference image. In the configuration, the switchover between the high-resolution view (narrow radiation range) and the low-resolution view (wide radiation range) can be effected only by manipulating the foot switch device 404, and therefore, the X-ray diagnosis apparatus realizes operations with intuitive actions. Note that the low-resolution view may also be called a "normal view".

Second Embodiment

An X-ray diagnosis apparatus according to the second embodiment will be described, with main reference to FIGS. 9 and 10 and with a focus on portions differing from the first embodiment.

The display device 400 according to this embodiment includes only a single monitor 405, unlike in the first embodiment. Instead, the monitor 405 is adapted to display a first window 405a and a second window 405b as shown in FIG. 9 ($\alpha$). The first window 405a functions as a first display area in a similar manner to the display screen of the first monitor 401 in the first embodiment. The second window 405b functions as a second display area in a similar manner to the display screen of the second monitor 402 in the first embodiment.

The X-ray diagnosis apparatus according to the second embodiment includes a control system as shown in FIG. 10. In the foregoing first embodiment, the control circuitry 500 takes control so that image data for one image is acquired from the X-ray image generating circuitry 302 or read from the storage circuitry 501 to generate one display image, and this display image is displayed on the first monitor 401 or the second monitor 402. On the other hand, under the control of the control circuitry 500 according to the present embodiment, image data for two images, i.e., one narrow-range image and one wide-range image, is acquired from the X-ray image generating circuitry 302 or read from the storage circuitry 501 to generate and display one final image. More specifically, the control circuitry 500 generates one final image in which one of the narrow-range image and the wide-range image is arranged in the first window 405a and the other one is arranged in the second window 405b, and displays this final image on the monitor 405.

How to determine the images to be displayed through the first window 405a and the second window 405b follows the determination method described above (cf. FIGS. 7A and 7B), with the first monitor 401 and the second monitor 402 replaced by the first window 405a and the second window 405b, respectively.

Figure 9:
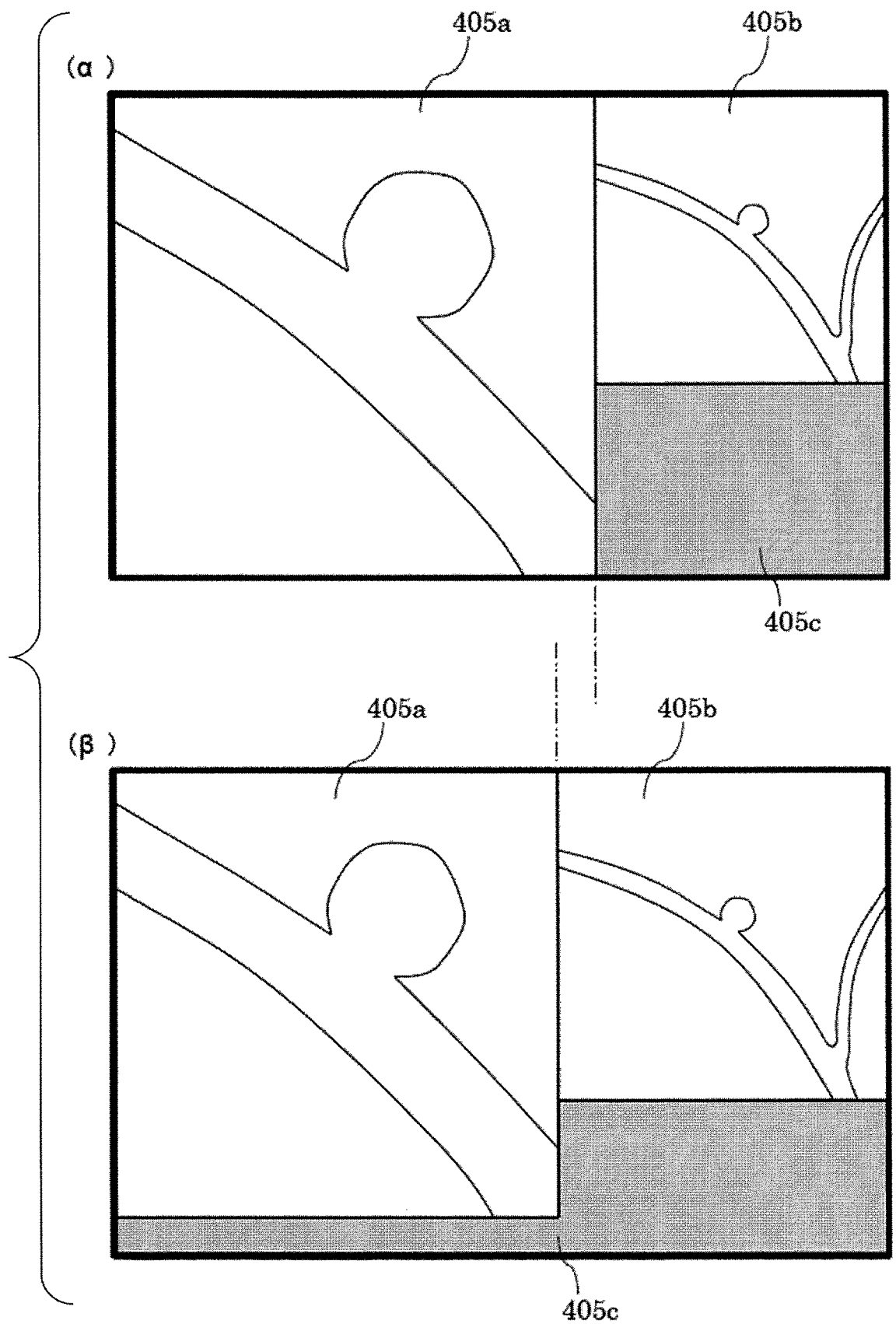
FIG. 9 is a diagram showing how displays are given on a monitor according to a second embodiment.

For example, the first window 405a and the second window 405b are given side by side, as shown in FIG. 9 (α). The second window 405b may be smaller than the first window 405a in the display, so that there is a text window 405c for presenting information about imaging conditions, etc., below the second window 405b.

The ratio by size between the first window 405a and the second window 405b can be changed by an operation at the console 118. This operation may be, for example, dragging the frame portion of the second window 405b.

In response to the operation of changing the size ratio between the first window 405a and the second window 405b, the sizes of the respective windows are adjusted with respect to the horizontal width of the display area of the monitor 405. For example, upon performing an operation for enlarging the second window 405b from the initial state shown in FIG. 9 (α), the size of the second window 405b is increased and the size of the first window 405a is decreased as shown in FIG. 9 (β). More specifically, the second window 405b is enlarged with its aspect ratio maintained, and concurrently, the first window 405a is shrunk with its aspect ratio maintained, based on the horizontal width of the display area serving as a sum of the entire widths of the first window 405a and the second window 405b. With this configuration, the size of the first window 405a can be maximized while meeting the conditions that the initial aspect ratios of the respective images are unchanged, the first window 405a and the second window 405b do not overlap with each other, and the first window 405a and the second window 405b are displayed on the monitor 405 in their entirety.

In the course of this example, the text window 405c is displayed also in the area created below the first window 405a. Therefore, the enlargement of the second window 405b does not diminish the text window 405c, and the text representation, etc., in the text window 405c do not need to use omissions or reduced font sizes.

Besides the display forms discussed, it is also possible to adopt a setting that tolerates the first window 405a and the second window 405b overlapping with each other, a setting that conforms the sizes of the first window 405a and the second window 405b to each other, and so on. The X-ray diagnosis apparatus according to this embodiment can provide the same advantages as in the first embodiment, including the capability of presenting substantially fresh images based on two radiation ranges (i.e., the wide radiation range and the narrow radiation range) while achieving the reduction in dose of exposure of a subject, allowing a physician to continue treatment operations without the necessity of moving its gaze away from the first window 405a, and also allowing the staffs, etc., other than the physician, to recognize the progress of the treatment at a glance.

Also, the X-ray diagnosis apparatus according to the embodiment employs a single monitor adapted to display the first window 405a functioning as a first display area and the second window 405b functioning as a second display area. Thus, the X-ray diagnosis apparatus can additionally offer a high degree of freedom in the layout of image displays.

Moreover, the sizes of the first window 405a and the second window 405b are discretionarily variable, and therefore, it is possible to proceed with the treatment operations with the displays of the most suitable sizes selected in each treatment scene.

Still more, according to the configuration of the embodiment, when one of the first window 405a and the second window 405b is enlarged, the size of the other is determined based on the width of the display area as a sum of the entire widths of the first window 405a and the second window 405b in the direction of their arrangement (e.g., horizontal direction). This allows for the effective use of the display screen of the monitor 405.

Third Embodiment

An X-ray diagnosis apparatus according to the third embodiment will be described, with main reference to FIGS. 11 to 13 and with a focus on portions differing from the first embodiment.

Figure 11:
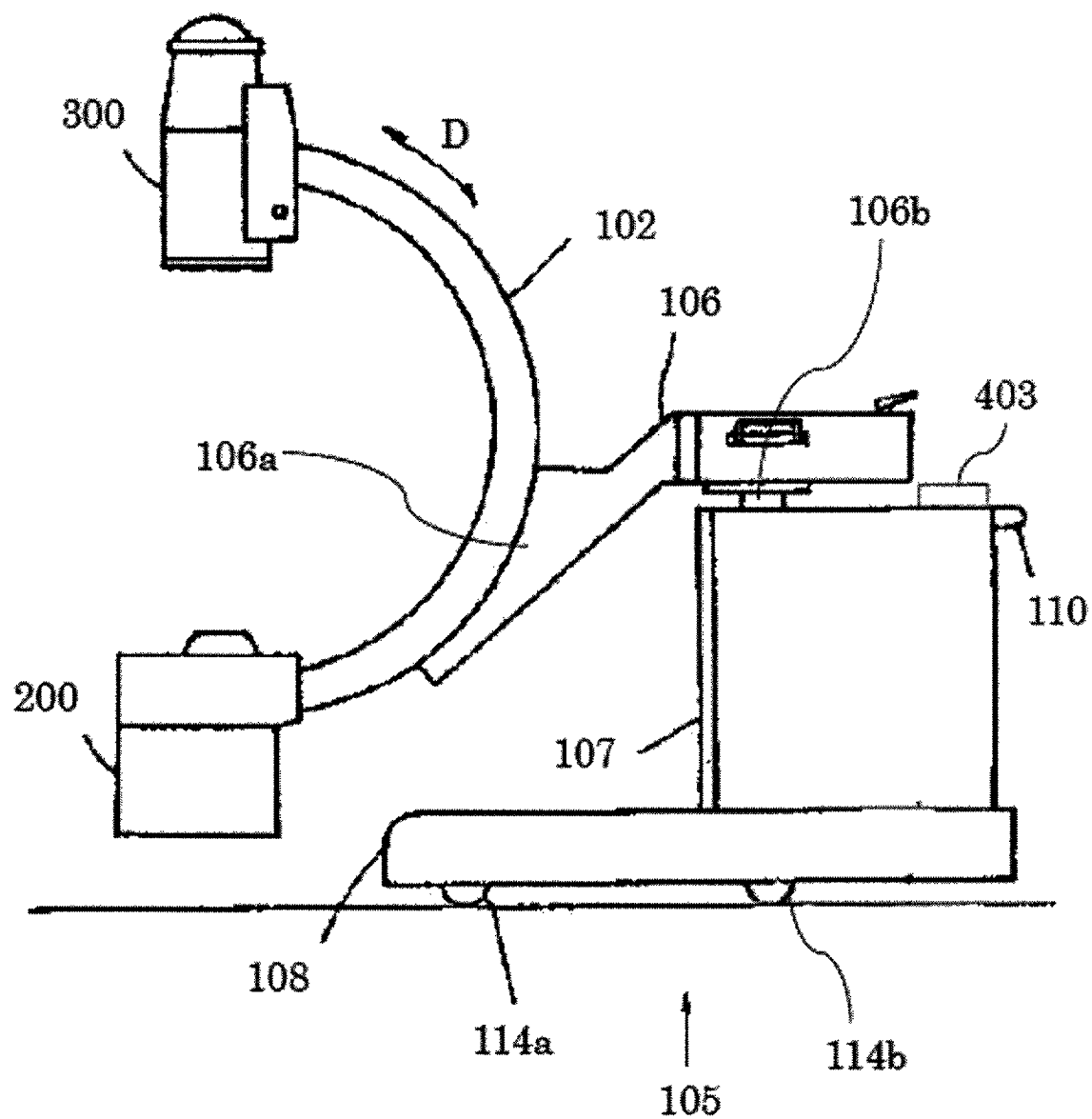
FIG. 11 is a side view of the external design of a C-arm wagon device according to a third embodiment.

The X-ray diagnosis apparatus according to this embodiment includes a C-arm wagon device 105 as shown in FIG. 11. The C-arm wagon device 105 includes a box 107, the supporting mechanism 106, the C-arm 102, the X-ray generating device 200, the X-ray detecting device 300, a base plate 108, and an operation panel 403.

The box 107 accommodates control circuitry 503, the storage circuitry 501, etc. (cf. FIG. 12). The control circuitry 503 has a radiation controlling function 503a for controlling the X-ray generating device 200 based on inputs from the foot switch device 404, etc., in a similar manner to the control circuitry 500 according to the first embodiment. The control circuitry 503, however, does not have a display image generating function for generating images to be displayed on the first monitor 401 or the second monitor 402 based on the image data received from the X-ray detecting device 300 or the storage circuitry 501.

The supporting mechanism 106 includes a connecting part 106a at one end, which is connected with the C-arm 102, and another connecting part 106b at the other end, which is connected with the box 107. The connecting part 106b on the side of the box 107 may be a vertical axis member adapted to enable the supporting mechanism 106 to rotate around it. The connecting part 106b is also adapted to change its length in the vertical direction so that the supporting mechanism 106 can be brought to various heights. The connecting part 106a is adapted to support the C-arm 102 so that the C-arm 102 can be driven in the direction D along its arc. The supporting mechanism 106 may be called a "supporting arm".

The C-arm 102, as in the first embodiment, holds the X-ray generating device 200 and the X-ray detecting device 300 at its respective ends.

The base plate 108 forms the bottom portion of the C-arm wagon device 105. The base plate 108 includes one or more casters 114a on the front side of the C-arm wagon device 105 (left in FIG. 11), and one or more casters 114b on the rear side (right in FIG. 11). While not shown in FIG. 11, there may be other casters behind the casters 114a and 114b (in the depth direction of FIG. 11). These casters enable the movement of the C-arm wagon device 105 with the use of a handle 110 at the rear of the box 107. Also, the front-side casters including the caster 114a are adapted to rotate around their respective vertical axes, so that the movement of the C-arm wagon device 105 can be turned to any directions.

The operation panel 403 may be attached to the upper rear portion of the C-arm wagon device 105, and is adapted to receive operational inputs for setting the radiation range, changing the X-ray intensity, etc. The operation panel 403 will be described in more detail later.

The X-ray diagnosis apparatus according to this embodiment includes a monitor wagon device 112 as shown in FIG. 13. The monitor wagon device 112 includes a box 113, the display device 400, an input device 409, and storage circuitry 505.

Figure 12:
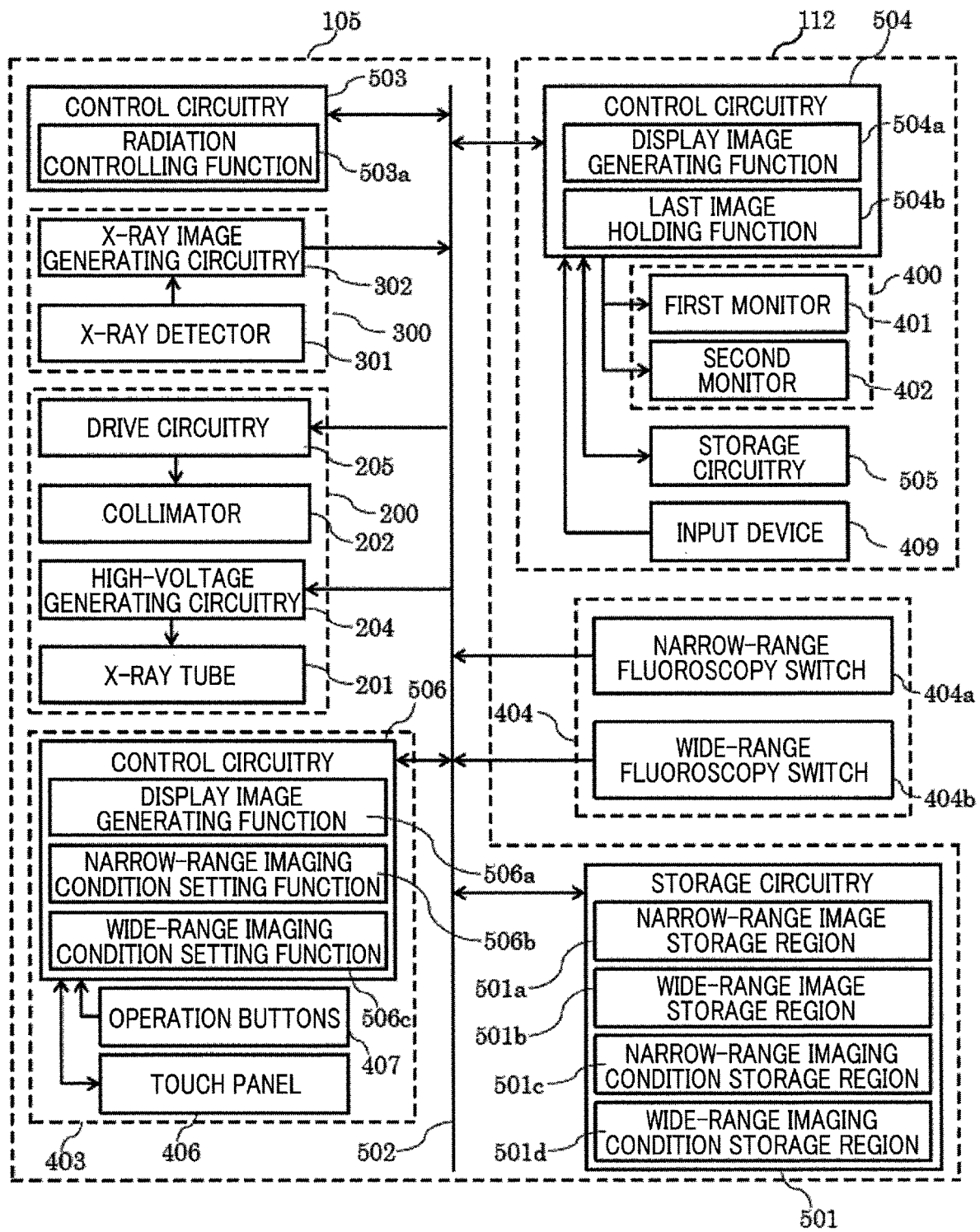
FIG. 12 is a functional block diagram showing a control system according to the third embodiment.

The box 113 accommodates control circuitry 504, and the storage circuitry 505 (cf. FIG. 12). The control circuitry 504 has a display image generating function 504a for generating images to be displayed on the first monitor 401 or the second monitor 402, based on the image data received from the X-ray detecting device 300 or the storage circuitry 501. The control circuitry 504 also has a last image holding function 504b. That is, among the functions of the control circuitry 500 according to the first embodiment, the radiation controlling function is realized by the control circuitry 503 on the side of the C-arm wagon device 105, and the display image generating function and the last image holding function are realized by the control circuitry 504 on the side of the monitor wagon device 112. Similar to the control circuitry 500 according to the first embodiment, the control circuitry 504 takes control over the displays on the first monitor 401 and the second monitor 402 of the display device 400, in accordance with the flowchart of FIGS. 7A and 7B. The control circuitry 503 and the control circuitry 504 constitute another example of the "processing circuitry".

The box 113 is provided with casters 113a and 113b and other casters (not shown in the figure; arranged in the depth direction of the figure) for enabling the movement of the monitor wagon device 112 with the use of a handle 115 at the rear of the box 113, as in the C-arm wagon device 105 above. Also, similar to the above, the casters 113a and 113b are adapted to rotate around their respective vertical axes, so that the movement of the monitor wagon device 112 can be turned to any directions.

The display device 400 is provided above the box 113 via a support 116, and includes the first monitor 401 and the second monitor 402 as in the first embodiment. The support 116 is adapted to change its length in the vertical direction and rotate around the vertical axis, so that the display device 400 can be arranged in a position and orientation that enhance the viewability. The display device 400 according to this embodiment is another example of the "display".

The input device 409 includes a keyboard 409a and a mouse 409b, and a user can perform operations such as changing the display setting for the display device 400, saving images, etc., through the input device 409. Changes of the display setting may include, for example, an interchange of the functions between the first monitor 401 and the second monitor 402. That is, the second monitor 402 may be used for displaying the latest images, and the first monitor 401 may be used for displaying last images that accompany the switchover of the radiation ranges. This allows for the selection of displays appropriate for the locations of the staffs or devices in the test room. Note that the setting to interchange the functions of the first monitor 401 and the second monitor 402 may also be input from the operation panel 403.

Additionally, when it is desired to save images, it is possible to relieve the second monitor 402 of the last-image holding state and instead have it serve as an image selection screen. In this manner, the first monitor 401 is kept displaying the latest images, and therefore, the treatment can proceed even while an assistant or the like is performing image saving operations.

The storage circuitry 505 is a storage component for storing data about the display setting for the display device 400, etc. For example, the storage circuitry 505 stores the setting to interchange the functions of the first monitor 401 and the second monitor 402 as discussed above, parameter setting for parallel display with acquired images, and so on. Note that the storage circuitry 505 may reserve a storage space for use as the narrow-range image storage region 501a, the wide-range image storage region 501b, and other storage regions, in lieu of the storage circuitry 501.

Figure 14:
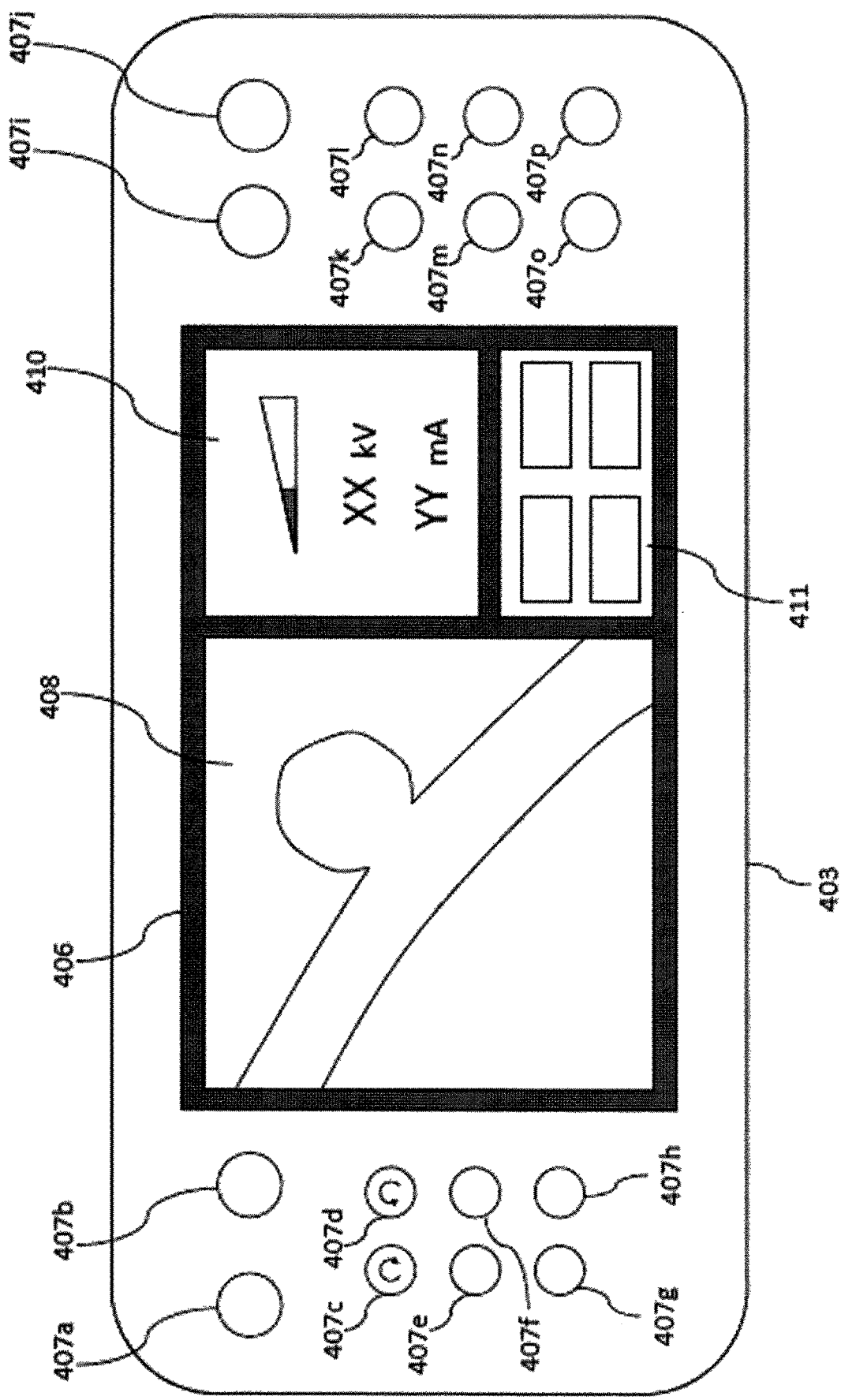
FIG. 14 is a plan view of an operation panel according to the third embodiment.

FIG. 14 shows the operation panel 403 including a touch panel 406 and operation buttons 407a to 407p. The touch panel 406 is a so-called projected capacitive-type touch-panel that combines two electrode films and a liquid crystal display. In the fluoroscopy mode, the touch panel 406 displays an image display window 408, a parameter display window 410, and an operation window 411. The image display window 408 always provides the latest image displays as the first monitor 401.

Among the operation buttons 407a to 407p, the operation buttons 407c and 407d may accept operations to turn the image displayed on the display device 400 in a clockwise or anti-clockwise manner. When the operation button 407c is pressed down, the images displayed on the first monitor 401 and the second monitor 402 turn clockwise, but the image in the image display window 408 on the touch panel 406 does not turn. Also, when the operation button 407d is pressed down, the images displayed on the first monitor 401 and the second monitor 402 turn anti-clockwise, but the image in the image display window 408 on the touch panel 406 does not turn. That is, in the instance where the first monitor 401 and the image display window 408 are caused to display images based on the same X-ray image data, the first monitor 401 displays the image having been subjected to the turn processing, while the image display window 408 displays the image without the turn processing. This configuration allows the assistant, etc., operating the operation panel 403, to easily and intuitively comprehend which radiation range has been irradiated with what amount of X-rays throughout the treatment, and accordingly, the dose of exposure can be readily managed.

With reference to FIG. 12, how the display of images in the image display window 408 on the touch panel 406 is controlled will be described. Images to be displayed in the image display window 408 and the images to be displayed on the first monitor 401 are based on the same data. The operation panel 403 includes control circuitry 506 adapted to acquire the same data as the data for the image to be displayed on the first monitor 401, in the manner similar to the control circuitry 504 acquiring the image data from the X-ray image generating circuitry 302 or the storage circuitry 501 for the display on the first monitor 401. The control circuitry 506 then generates an image based on this data for the display in the image display window 408, independently of the control circuitry 504. In other words, the control circuitry 506 has a display image generating function 506a, separate from the display image generating function 504a of the control circuitry 504 of the monitor wagon device 112.

Figure 7A:
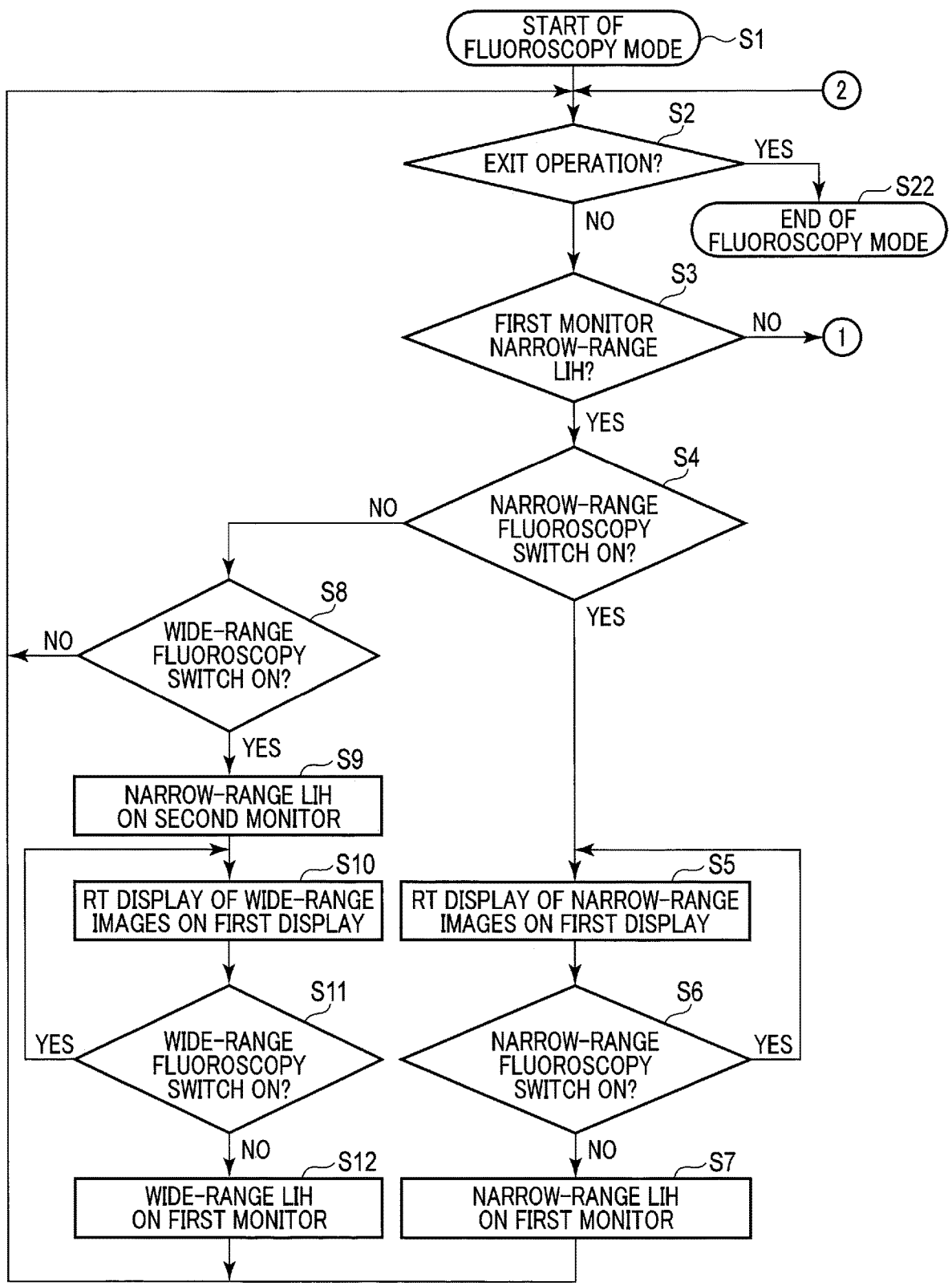
FIG. 7A is a flowchart showing control under a fluoroscopy mode according to the first embodiment.
Figure 7B:
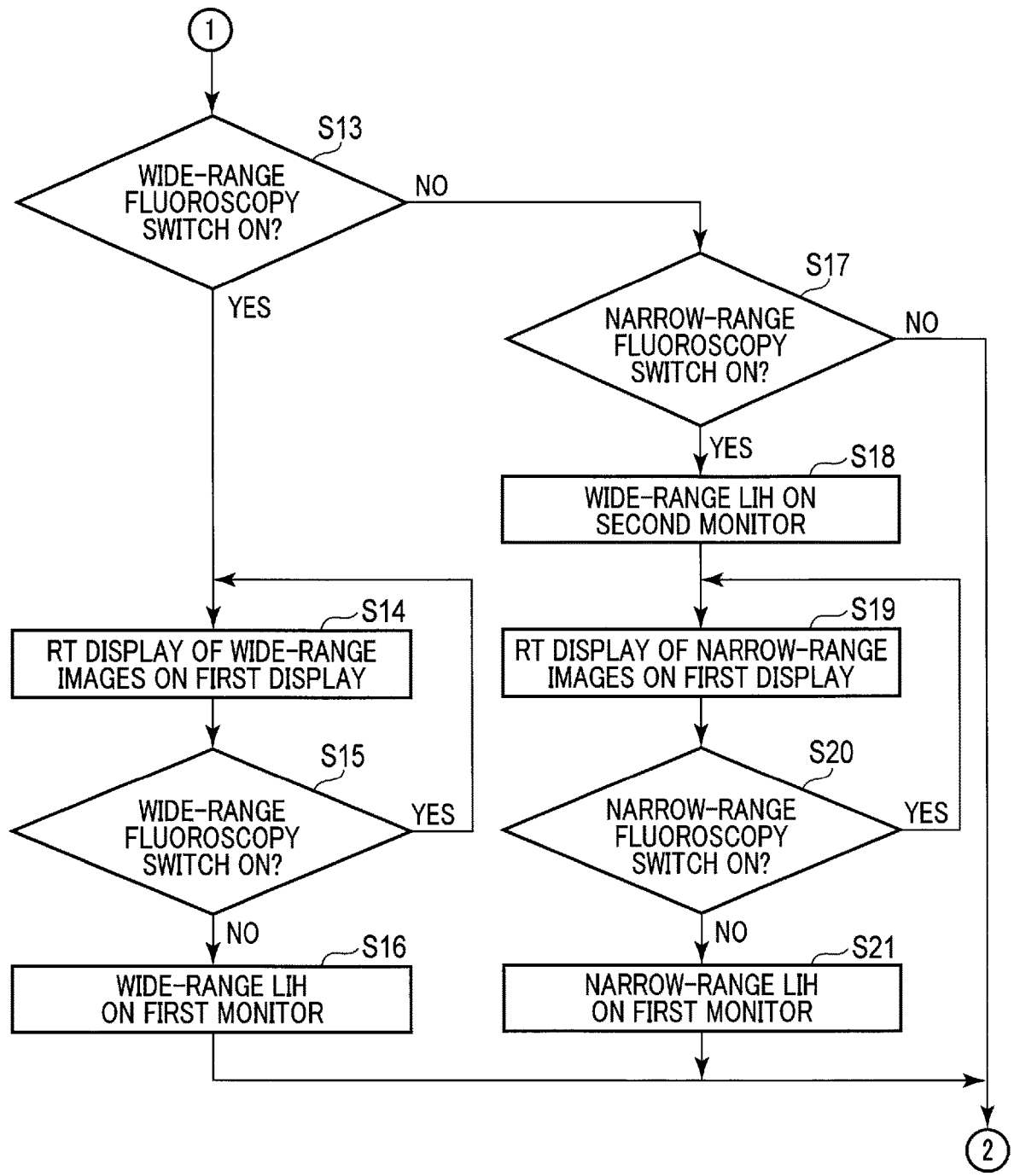
FIG. 7B is the flowchart showing control under the fluoroscopy mode according to the first embodiment.

For the period of halt of the X-ray radiations, the control circuitry 504 of the monitor wagon device 112 causes the first monitor 401 and the second monitor 402 to display the images by following the control flow as in the first embodiment (cf. FIGS. 7A and 7B). Meanwhile, the control circuitry 506, for the touch panel 406, acquires the same data as the data used for the display on the first monitor 401 from the X-ray image generating circuitry 302, or reads it from the storage circuitry 501. The control circuitry 506 also generates the display image for the touch panel 406 based on the acquired data or the read data, and displays it through the image display window 408.

Description will be given of the display control for the display device 400 when the operation button 407c or 407d is pressed down. As discussed, the control circuitry 504 of the monitor wagon device 112 generates the display image for the display device 400 based on the image data from the X-ray image generating circuitry 302 or the storage circuitry 501, and causes the first monitor 401 or the second monitor 402 to display this display image. In the context of this processing, when the operation button 407c is pressed down, the control circuitry 504 performs a clockwise turn transform processing on the image data so as to obtain new image data, and generates a display image based on this new image data for the display on the first monitor 401 or the second monitor 402. Also, when the operation button 407d is pressed down, the control circuitry 504 performs an anti-clockwise turn transform processing on the image data from the X-ray image generating circuitry 302 or the storage circuitry 501 so as to obtain new image data, and generates a display image based on this new data for the display on the first monitor 401 or the second monitor 402.

The X-ray diagnosis apparatus according to this embodiment can provide the same advantages as in the first embodiment, including the capability of presenting substantially fresh images based on two radiation ranges (i.e., the wide radiation range and the narrow radiation range) while achieving the reduction in dose of exposure of a subject, allowing a physician to continue treatment operations without the necessity of moving its gaze away from the first monitor 401, and also allowing the staffs, etc., other than the physician, to recognize the progress of the treatment at a glance.

According to the embodiment, moreover, when turning an image on the display device 400 viewed by a physician, the image on the operation panel 403 used by an assistant is not turned. This configuration allows the assistant to easily manage the dose of exposure.

Other Embodiments

The first to third embodiments have been described, assuming that the X-ray detector having multiple detecting parts of different spatial resolutions is employed, but an X-ray detector having a single-resolution detecting part may instead be employed. In this instance, the wide-range imaging may be performed with a binning number larger than that in the narrow-range imaging. This enables the setting of X-ray conditions according to the magnifying ratio of images on the display part, and can consequently reduce the dose of exposure of a subject.

The first to third embodiments adopt a configuration in which the image data output from the X-ray image generating circuitry 302 is continuously stored in the storage circuitry 501 by overwriting the older data, but a certain set of image data may be accumulated therein instead of performing such overwrite save. For example, data corresponding to several last images may be accumulated for each of the wide and narrow radiation ranges.

Also, the first to third embodiments may adopt a configuration in which the storage circuitry 501 does not store the image data output from the X-ray image generating circuitry 302 for the period of the narrow-range fluoroscopy switch 404a or the wide-range fluoroscopy switch 404b being stepped on, and the storage circuitry 501 stores the image data only upon separation of the foot from the narrow-range fluoroscopy switch 404a or the wide-range fluoroscopy switch 404b.

Furthermore, in the configuration of the first to third embodiments that transfers the last image displayed on the first display area (the first monitor 401 or the first window 405a) to the second display area (the second monitor 402 or the second window 405b) in response to the switchover of the radiation range, the last image to be displayed on the second display area does not have to be identical the last image having been displayed on the first display area. That is, the second display area may use an image of a frame timing that differs by several to several tens of frames from the image having been displayed on the first display area, or an image which has been subjected to different image processing.

The first to third embodiments employ, as the "last image from the narrow-range imaging", the most recent image among the images acquired from the imaging with the small radiation range. The embodiments may instead employ an image acquired in advance of the most recent image, as long as such an image can be equated to the most recent image. For example, use of an image which is several to several tens of frames prior to the most recent image is possible. Likewise, as the "last image from the wide-range imaging", the embodiments may replace the most recent image among the images acquired with the large radiation range, with an image acquired in advance of this most recent image.

Furthermore, the first to third embodiments may assign the functions of the respective control circuitry to any other control circuitry. For example, in the first embodiment, the narrow-range imaging condition setting function 507b, the wide-range imaging condition setting function 507c, etc., may be assigned to the control circuitry 500. Also, the components for which the inclusion of control circuitry is not intended in the first to third embodiments may include control circuitry, and such control circuitry may have the functions of the respective control circuitry described for the first to third embodiments.

The first to third embodiments may assign the storage regions of the respective memory circuitry to any other storage circuitry. Also, the components for which the inclusion of storage circuitry is not intended in the first to third embodiments may include storage circuitry, and such storage circuitry may include the storage regions of the respective storage circuitry described for the first to third embodiments.

Furthermore, the two radiation ranges as the subjects of switchover in the first to third embodiments may be set to the same area, with the centers of the respective radiation ranges displaced from each other.

Additionally, it has been described for the third embodiment that it can adopt a configuration of interchanging the functions of the first monitor 401 and the second monitor 402 in response to an input to the input device 409. This configuration is applicable to the first embodiment and the second embodiment, as well. More specifically, the first embodiment may adopt a configuration of interchanging the functions of the first monitor 401 and the second monitor 402 in response to an input to the input device 412. The second embodiment may adopt a configuration of interchanging the positions of the first window 405a and the second window 405b in response to an input to the input device 412.

The term "processor" used in the foregoing description refers to, for example, a central processing unit (CPU) or a graphics processing unit (GPU), or various types of circuitry which may be an application-specific integrated circuit (ASIC), a programmable logic device (such as a simple programmable logic device (SPLD), a complex programmable logic device (CPLD), or a field programmable gate array (FPGA)), and so on. The processor reads programs stored in the storage circuitry and executes them to realize the respective functions. The programs may be incorporated directly in circuits of the processor, instead of being stored in the storage circuitry. In this case, the processor reads the programs incorporated in its circuits and executes them to realize the functions. The embodiments do not limit the processor to a single circuitry-type processor. A plurality of independent circuits may be combined and integrated as one processor having multiple functions.

The term "storage component" used in the foregoing description refers to, for example, not only a main storage device constituted by a DRAM, an SRAM, an MRAM, or the like, but also an auxiliary storage device constituted by a flash memory, a hard disk drive (HDD), or the like. Also, the storage circuitry in the foregoing embodiments may be constituted by a multiple of the storage components. In this case, the individual storage components do not have to be physically put together in one location. Furthermore, the individual storage components in this case may be arranged on discrete hardware members which are connected by wire or wirelessly to each other.

According to at least one embodiment having been discussed, at the time of switching the X-ray radiation ranges, the last image acquired from the radiation range up to the switchover is kept displayed after the switchover. With this configuration, it is possible to present substantially fresh images based on two radiation ranges, i.e., the wide radiation range and the narrow radiation range, while achieving the reduction in dose of exposure of a subject.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray diagnosis apparatus comprising:
an X-ray tube configured to generate X-rays;
a diaphragm mechanism configured to limit a radiation range of the X-rays;
an X-ray detector facing the X-ray tube and configured to detect the X-rays;
image generating circuitry configured to sequentially generate X-ray images based on outputs from the X-ray detector;
a display comprising a first display area and a second display area;
a first interface and a second interface configured to receive an operation from an operator; and
processing circuitry configured to control the diaphragm mechanism and the X-ray tube according to the operation to the first interface so that the X-rays are radiated to a first radiation range, control the diaphragm mechanism and the X-ray tube according to the operation to the second interface so that the X-rays are radiated to a second radiation range, and control the display so that the first display area displays the X-ray images sequentially generated according to radiation of the X-rays, in parallel with the radiation,
wherein one of the first radiation range and the second radiation range encompasses remaining one of the first radiation range and the second radiation range,
wherein the processing circuitry is configured to control the display so that,
in response to (1) a switchover of the radiation range from the first radiation range to the second radiation range for further radiation of the X-rays after the radiation to the first radiation range,
the first display area displays the X-ray images sequentially generated according to the further radiation to the second radiation range, in parallel with the further radiation, and
the second display area displays an image based on the X-ray images having been generated according to the radiation to the first radiation range and displayed on the first display area,
wherein the first display area displays the X-ray images newer than the image displayed on the second display area no matter whether the X-rays are being radiated or not radiated, and wherein the first display area displays the newer X-ray images in real time when the X-rays are being radiated, and
in response to (1) a switchover of the radiation range from the first radiation range to the second radiation range for further radiation of the X-rays after the radiation to the first radiation range, (2) a stop of the operation to the second interface after the further radiation, and subsequently (3) another operation to the second interface for another radiation to the second radiation range,
the first display area displays an X-ray image based on said another radiation to the second radiation range, in parallel with said another radiation, and
the second display area keeps displaying the image based on the X-ray images having been generated according to the radiation to the first radiation range and displayed on the first display area.

2. The X-ray diagnosis apparatus according to claim 1, wherein the processing circuitry is configured to control the display so that, when the X-rays are radiated to the first radiation range after the further radiation to the second radiation range, the first display area sequentially displays the X-ray images generated according to ongoing radiation to the first radiation range, and the second display area displays an image based on the X-ray images having been generated according to the further radiation to the second radiation range and displayed on the first display area.

3. The X-ray diagnosis apparatus according to claim 1, wherein the image displayed on the second display area is a still image generated most recently among the X-ray images having been generated according to the radiation.

4. The X-ray diagnosis apparatus according to claim 3, wherein the X-ray images generated according to radiation to the first radiation range have a higher spatial resolution than the X-ray images generated according to radiation to the second radiation range.

5. The X-ray diagnosis apparatus according to claim 3, wherein
the X-ray detector comprises an X-ray detecting portion including a high-resolution detecting part and a lower resolution part, the high-resolution detecting part having a higher pixel density than said lower resolution part, the first radiation range is covered by the high-resolution detecting part, the second radiation range is larger than the high-resolution detecting part, and the image generating circuitry is configured to generate, in response to the operation to the first interface, the X-ray images using outputs from the high-resolution detecting part, without using outputs from said lower resolution part, and to generate, in response to the operation to the second interface, the X-ray images using at least the outputs from said lower resolution part.

6. The X-ray diagnosis apparatus according to claim 5, wherein the first interface and the second interface are configured as a first switch and a second switch in an operation unit, respectively, wherein the operation unit is adapted to receive the operation via a foot of the operator.

7. The X-ray diagnosis apparatus according to claim 1, wherein the X-ray images generated according to radiation to the first radiation range have a higher spatial resolution than the X-ray images generated according to radiation to the second radiation range.

8. The X-ray diagnosis apparatus according to claim 1, wherein the X-ray detector comprises an X-ray detecting portion including a high-resolution detecting part and a lower resolution part, the high-resolution detecting part having a higher pixel density than said lower resolution part, the first radiation range is covered by the high-resolution detecting part, the second radiation range is larger than the high-resolution detecting part, and the image generating circuitry is configured to generate, in response to the operation to the first interface, the X-ray images using outputs from the high-resolution detecting part, without using outputs from said lower resolution part, and to generate, in response to the operation to the second interface, the X-ray images using at least the outputs from said lower resolution part.

9. The X-ray diagnosis apparatus according to claim 1, wherein the first interface and the second interface are configured as a first switch and a second switch in an operation unit, respectively, wherein the operation unit is adapted to receive the operation via a foot of the operator.

10. The X-ray diagnosis apparatus according to claim 2, wherein the X-ray images generated according to radiation to the first radiation range have a higher spatial resolution than the X-ray images generated according to radiation to the second radiation range.

11. The X-ray diagnosis apparatus according to claim 2, wherein the X-ray detector comprises an X-ray detecting portion including a high-resolution detecting part and a lower resolution part, the high-resolution detecting part having a higher pixel density than said lower resolution part, the first radiation range is covered by the high-resolution detecting part, the second radiation range is larger than the high-resolution detecting part, and the image generating circuitry is configured to generate, in response to the operation to the first interface, the X-ray images using outputs from the high-resolution detecting part, without using outputs from said lower resolution part, and to generate, in response to the operation to the second interface, the X-ray images using at least the outputs from said lower resolution part.

12. The X-ray diagnosis apparatus according to claim 2, wherein the first interface and the second interface are configured as a first switch and a second switch in an operation unit, respectively, wherein the operation unit is adapted to receive the operation via a foot of the operator.

13. The X-ray diagnosis apparatus according to claim 3, wherein the first interface and the second interface are configured as a first switch and a second switch in an operation unit, respectively, wherein the operation unit is adapted to receive the operation via a foot of the operator.

14. The X-ray diagnosis apparatus according to claim 4, wherein the first interface and the second interface are configured as a first switch and a second switch in an operation unit, respectively, wherein the operation unit is adapted to receive the operation via a foot of the operator.

* * * * *